United States Patent
Bagur et al.

(10) Patent No.: US 11,415,654 B2
(45) Date of Patent: Aug. 16, 2022

(54) METHOD OF ANALYSING MAGNETIC RESONANCE IMAGING IMAGES

(71) Applicants: Perspectum Limited, Oxford (GB); Alexandre Bagur, Oxford (GB); Chloe Hutton, Oxford (GB); Benjamin J Irving, Oxford (GB); Michael L Gyngell, Oxford (GB); Matthew Robson, Oxford (GB); Michael J Brady, Oxford (GB)

(72) Inventors: Alexandre Bagur, Oxford (GB); Chloe Hutton, Oxford (GB); Benjamin J Irving, Oxford (GB); Michael L Gyngell, Oxford (GB); Matthew Robson, Oxford (GB); Michael J Brady, Oxford (GB)

(73) Assignee: Perspectum Limited, Oxford (GB)

( * ) Notice: Subject to any disclaimer, the term of this patent is extended or adjusted under 35 U.S.C. 154(b) by 0 days.

(21) Appl. No.: 17/272,671

(22) PCT Filed: Sep. 4, 2019

(86) PCT No.: PCT/EP2019/073545
§ 371 (c)(1),
(2) Date: Mar. 2, 2021

(87) PCT Pub. No.: WO2020/049025
PCT Pub. Date: Mar. 12, 2020

(65) Prior Publication Data
US 2021/0270919 A1   Sep. 2, 2021

(30) Foreign Application Priority Data
Sep. 4, 2018 (GB) .................... 1814358

(51) Int. Cl.
*G01V 3/00* (2006.01)
*G01R 33/48* (2006.01)
(Continued)

(52) U.S. Cl.
CPC .......... *G01R 33/4828* (2013.01); *A61B 5/055* (2013.01); *G01R 33/50* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| 8,957,681 B2 | 2/2015 | Hernando |
| 2013/0214781 A1 | 8/2013 | Hernando |

(Continued)

OTHER PUBLICATIONS

Alexandre Triay Bagur et al: 11 Magnitude-intrinsic water-fat ambiguity can be resolved with multipeak fat modeling and a multipoint search method11 , Magnetic Resonance in Medicine., vol. 82, No. 1, Mar. 15, 2019 (Mar. 15, 2019) , pp. 460-475, XP055624322, us ISSN: 0740-3194, DOI: 10.1002/mrm.27728.

(Continued)

*Primary Examiner* — Walter L Lindsay, Jr.
*Assistant Examiner* — Frederick Wenderoth
(74) *Attorney, Agent, or Firm* — Optimus Patents US, LLC

(57) ABSTRACT

A method of analysing the magnitude of Magnetic Resonance Imaging (MRI) data is described. The method comprising: using the magnitude only of the multi-echo MRI data of images from the subject, where images are acquired at arbitrarily timed echoes including at least one echo time where water and fat are not substantially in-phase; fitting the magnitude of said multi-echo MRI data to a single signal (Continued)

(a)

(b)

(c)

model to produce a plurality of potential solutions for the relative signal contributions for each of the at least two species from the model, by using a plurality of different starting conditions to generate a particular cost function value for each of the plurality of starting conditions, where said cost function values are independent of a field map term for the MRI data; analysing said cost function values to calculate relative signal separation contribution for each species at each voxel of the images.

20 Claims, 14 Drawing Sheets

(51) Int. Cl.
*A61B 5/055* (2006.01)
*G01R 33/50* (2006.01)
*G01R 33/561* (2006.01)
*G06T 7/00* (2017.01)

(52) U.S. Cl.
CPC ........ *G01R 33/5615* (2013.01); *G06T 7/0012* (2013.01); *G06T 2207/10096* (2013.01)

(58) Field of Classification Search
USPC ........................................................ 324/309
See application file for complete search history.

(56) References Cited

U.S. PATENT DOCUMENTS

| | | | |
|---|---|---|---|
| 2013/0221961 A1* | 8/2013 | Liu | G01R 33/56545 324/307 |
| 2015/0123658 A1 | 5/2015 | Zhong | |
| 2017/0345149 A1 | 11/2017 | Warntjes | |
| 2018/0132787 A1 | 5/2018 | Leporq | |

OTHER PUBLICATIONS

Alexandre Triay Bagur et al: "Field Map Estimation from Magnitude-Based Water-Fat Separation", Proceedings of the International Society for Magnetic Resonance in Medicine, 27th Annual Meeting and Exhibition, Montreal, QC, Canada, May 11-16, 2019, Apr. 26, 2019 (Apr. 26, 2019), p. 4381, XP055642636, the whole document.

Bydder et al: "Relaxation effects in the quantification of fat using gradient echo imaging", Magnetic Resonance Imaging, Elsevier Science, Tarrytown, NY, US, vol. 26, No. 3, Feb. 21, 2008 (Feb. 21, 2008), pp. 347-359, XP022511971,ISSN: 0730-725Xcited in the application p. 348, col. 2-p. 352, col. 2.

* cited by examiner

METHOD OF ANALYSING MAGNETIC RESONANCE IMAGING IMAGES

FIELD OF INVENTION

This invention relates to a method of analysing Magnetic Resonance Imaging (MRI) images, particularly to the use of the MRI signal to separate out the contributions of different chemical species, such as water and fat and proton density fat fraction (PDFF) estimation.

BACKGROUND OF INVENTION

The data that forms an MRI image is collected in a representation known as k-space; a mathematical process known as Fourier Transform is then applied to this k-space representation in order to yield the MRI image. The Fourier Transform yields values that are complex numbers, comprising a real part $R(x,y)$ and an imaginary part $I(x,y)$. Often, these are combined to form the Magnitude $M(x,y) = \sqrt{R^2(x,y) + I^2(x,y)}$, though there has also been a great deal of previous work using the phase $\phi(x,y) = \arctan(I(x,y)/R(x,y))$. Evidently, the magnitude and phase can be computed from the real and imaginary values; conversely, the real and imaginary values can be calculated from the magnitude and phase values.

The MRI image will be made up of a collection of voxels. The MRI image data can be analysed to determine the amount of water $w(x)$ and the amount of fat $f(x)$ (or other species) for each voxel x, of the image assuming that those are the only types of tissue in that voxel. These values can be used to report a ratio $PDFF(x)$ (proton density fat fraction). The estimation of w, f, PDFF are impacted by the spatially varying field $B_0(x)$ or $\psi(x)$ as given later.

Multi-echo chemical-shift encoded (CSE) water-fat separation MRI methods are increasingly reliable and reproducible for complete fat suppression and for proton density fat fraction (MRI-PDFF) quantification. These methods exploit the differences in the precession frequencies of water and fat to estimate fat content and have been validated against histological steatosis grading and spectroscopy measures (refs 1-23).

To date, most advanced CSE methods are complex-based, in that they use both the magnitude and phase of the MRI signal, and they calculate MRI-PDFF indirectly by first estimating a "field map" or "fieldmap", which is a measure of (essentially inevitable) $B_0$ inhomogeneity (refs 7,10,11, 13,16,17, 24-30). The water and fat contents at a voxel of an MRI image—and their ratio MRI-PDFF—may be uniquely determined provided a field map value is available. However, field map estimation is a non-trivial optimisation problem with multiple candidate solutions or local minima. Convergence is sensitive to initialisation and may, and often does, lead to inaccurate water and fat measures, often with mis-identification of the dominant species ('fat-water swap' artefacts). To mitigate this problem, a number of field map estimation algorithms use spatial regularization, though the implied smoothness may not hold in cases of poor shimming; local magnetic susceptibility (due to e.g. air-tissue interfaces); or hepatic iron overload.

Dixon (5) exploited the known differences in the precession frequencies of water and fat signals under a static magnetic field in order to obtain separate fat and water images. This was done by acquiring two images: one in which the water and fat signals are predicted to be in-phase; the other when they are predicted to be out-of-phase. The method relies upon the assumption that the static magnetic field is the same everywhere (a condition referred to as $B_0$ homogeneity). However, as has been widely reported in the literature, in clinical practice this assumption is not realistic. The inhomogeneous (i.e. spatially varying) $B_0$ is referred to as a 'fieldmap' and denoted mathematically as $\psi$.

To overcome this practical difficulty, Glover (31) presented a modified "3-pt Dixon" method that accounted for any $B_0$ inhomogeneity by making three acquisitions: one centred at the desired echo time; and two other acquisitions placed symmetrically before and after the echo time. However, it was shown by Reeder et al (11) that such symmetrically placed acquisitions have poor noise performance.

Reeder et al (11) and U.S. Pat. No. 7,176,683 describe the Iterative Decomposition of Water and Fat using Echo Asymmetry and Least Squares Estimation (IDEAL) method, by which asymmetric acquisitions are possible, increasing the noise performance of water-fat separation. Separation of water and fat from the acquired images comprises of two steps. First, the field map is estimated. Then, in a second step, a pixel-by-pixel iterative least squares method is first used to estimate the water and fat proportions at each pixel. This method uses a linear least squares estimation process that linearizes the non-linear equation into the two-step process.

Reeder also found (U.S. Pat. No. 7,508,211) that pixel values could be combined spatially using regularised species decomposition and presented an exemplary method in Yu et al., (24). This is based on a down-sampling followed by a region-growing scheme to correlate the estimation of the fieldmap among neighbouring pixels in order to obtain a 'trusted' fieldmap which then becomes the initial estimate for IDEAL processing. This approach assumes that the field map is slowly varying.

Fieldmap estimation algorithms are sometimes highly sensitive to the choice of starting "seed", (see the region-growing approach in Yu et al., (24)) and noise, which may lead to error propagation through space. Soliman et al., (29) discuss other methods to estimate the fieldmap, primarily by imposing a variety of smoothness conditions (Variable Projection (VARPRO), Joint Inhomogeneity estimation via Global Segment Assembly for Water-fat separation (JIG-SAW), Fat Likelihood Analysis for Multiecho Signals (FLAME)). They then present their own, Max-IDEAL, which relies on a max-flow algorithm to calculate an initial estimate of the fieldmap, which is then used in turn by IDEAL processing.

Yu et al., (17), Caussy et al., (3) and many others have asserted that it is necessary to use both a phase image and a magnitude image (the "complex" case) in order to obtain fat-water fraction estimates which cover the entire range of possible values, namely from 0% (water) to 100% (pure fat). They consider that if magnitude methods "alone" are used, then there is an inevitable fat-water ambiguity which will cause true fat-fraction values above 50% to become aliased to values below 50% (3, 15, 17). This assertion has now generally been accepted in the field.

Yu et al., (32) and U.S. Pat. No. 8,373,415 present the Fat Likelihood Analysis for Multi-echo Signals (FLAME) method that exploits information on the spectral complexity of fat to determine a 'fat likelihood' map using complex-sourced data and calculated fieldmap values from two signal models: a single-peak model and a multi-peak model. This methodology will produce multiple solutions. The fat likelihood map is combined with smoothness assumptions on the fieldmap and an iterative region-growing algorithm to resolve the water-fat ambiguity. However, the field map optimization space contains infinite minima and need not be periodic in the general case of asymmetric echoes. Furthermore, noise may corrupt the cost function values altering the global and local minima, leading to inaccurate fat fraction estimates.

U.S. Pat. No. 8,957,681 B2 describes that, in the particular case of in-phase and opposed-phase (IP/OP) echo acquisitions, the water-fat ambiguity is removed by fitting the magnitudes of the in-phase echoes only, provided that a fat model with multiple peaks is used. In a second sequential step, the out-of-phase echoes are used to refine and improve the signal-to-noise ratio of the image obtained in the first step that used in-phase echoes only. However, there are known disadvantages of using sequential IP/OP acquisitions, not least the long scanning times and their noise performance and its dependence on PDFF; these are much less of a concern with asymmetric echoes (11). Also, sequential IP/OP acquisitions lead to poor SNR in the case of fast signal decay (e.g., due to hepatic iron overload) because only a small number of echoes correspond to signal as opposed to noise (33).

U.S. Pat. No. 10,359,488 B2 and an example of that method in Zhong et al. (34) present a two-step procedure that aims to avoid fat-water swaps and that may use either complex or magnitude fitting. In the first step, a set of measured water and fat values (Mw1 and Mf1, respectively) are obtained. Then, these measured quantities are 'swapped' (Mw2=Mf1 and Mf2=Mw1) and their cost function is evaluated, and the set of measured water and fat values with better fit is chosen as the output of the method.

Other work, for example U.S. Pat. No. 10,359,488 B2, attempts to estimate relaxation properties of a tissue subject in a first step, such as R1, R2 or PD, and, in a second step, feeds these into a tissue model with fixed assumptions on water R1, R2 and PD, in order to identify contributions from tissue types different than water into the signal. In U.S. Pat. No. 10,359,488 B2, tissue separation is a post-processing step that entails empirical assumptions regarding the water relaxation parameters.

FIG. 1 illustrates various different MRI PDFF images obtained using different processing techniques. The top left-hand figure (a) shows an MRI image obtained using the known IDEAL methodology, using all the complex data, that is magnitude and phase data to produce the image. This image was also produced using a region growing regularisation algorithm, and shows that a region growing regularisation algorithm may be disadvantageous in particular cases, where there may be error propagation across image (a) resulting in fat-water swap artefacts; In those cases, the original IDEAL processing (image b), with no region growing regularisation may be used. Image (c) shows the image that results from the IDEAL processing methodology using only magnitude data Image (d) is the difference image, and as shown by the difference image (d), subcutaneous fat estimates are aliased to values below 50%. This causes the Magnitude-IDEAL method to be the last preferred option for data analysts and is the main reason magnitude-based methods are generally unpopular.

While complex-based (CSE) methods as discussed above are widely used, they assume the availability and reliability of phase images and, while this may be a reasonable assumption in a research setting, it is typically a challenge in general clinical practice with particular scanner manufacturers and models. This may preclude the use of a complex-based method as a single standardized cross-vendor approach. Generally, phase information is not easily available in clinical practice, or if it is available, it may not be reliable. This is due in part to the errors in the real and imaginary parts of the data. For example, if the error in the real part R(x, y) is dR, and the error in the imaginary part I(x, y) is dI, then the relative error in the phase data dP will be much larger that the relative error in the magnitude data dM.

For these reasons, magnitude-based (or magnitude-only) methods have been proposed. As well as being insensitive to phase errors, a major advantage of magnitude-based methods is they do not require prior field map estimation (or any related assumptions that may propagate errors), enabling direct MRI-PDFF estimation. However, the adoption of magnitude methods has been limited because of the belief that it is not possible to determine MRI-PDFF values above 50%: this is known as the magnitude-related water-fat ambiguity. In essence, fat-dominant pixels (e.g. subcutaneous fat regions in abdominal imaging) will be aliased to MRI-PDFF values below 50% and appear 'swapped', which (a) may mislead diagnosis when no previous information on the body being imaged is available, and (b) could undermine the confidence of clinicians taking account of hepatic fat estimates. However, since phase errors due to e.g. eddy currents may clinically impact MRI-PDFF measures, hybrid methods have been created: complex-based estimation may be used first to resolve MRI-PDFF over the full dynamic range (0-100%), then a magnitude-based estimation refines the estimates.

While fat-water fractions are almost always below 50% for voxels within the liver parenchyma, the fraction is generally much higher than 50% for voxels corresponding (for example) to visceral fat. In current practice, the calculation of fat-fraction estimates within the full dynamic range (0-100%) relies on using phase data and accurate fieldmap estimation. However, (i) phase distortions are often present in clinical practice, and/or (ii) phase information may either not be reliable, or, in many cases, simply not available. By comparison, magnitude data is always available and almost always reliable.

Bydder et al., (15) present different signal models with increasing levels of complexity that use only the magnitude data to estimate fat fraction. These models are subject to the known magnitude-related water-fat ambiguity.

Current species separation methods based on the magnitude of multi-echo signals require either (a) using at least two signal models during the fitting; (b) substantially in-phase echo times, or (c) prior knowledge about the subject being imaged (to avoid confusion between true converged values and aliased estimates).

SUMMARY OF THE INVENTION

According to example embodiments of a first aspect of the invention there is provided a method of analysing the magnitude of Magnetic Resonance Imaging (MRI) data from acquired MRI images of a subject, to determine the relative signal contributions of at least two species to each voxel of the images, the method comprising the steps of: using the magnitude of the multi-echo MRI data of images from the subject, where the images are acquired at arbitrarily timed echoes including at least one echo time where water and fat are not substantially in-phase with each other; fitting the magnitude of said acquired multi-echo MRI data to a single signal model to produce a plurality of potential solutions for the relative signal contributions for each of the at least two species from the model, by using a plurality of different starting conditions to generate a particular cost function value for each of the plurality of starting conditions, where said cost function values are independent of a field map term for the MRI data; and analysing said cost function values to calculate the relative signal separation contribution for each species at each voxel of the images.

Preferably, said analysis of said cost function values comprises the step of: comparing the generated cost function values to determine which is the correct solution for said signal separation.

Further preferably, the lowest cost function value of said species is determined to be the correct solution for said signal.

In an example of the invention the magnitude of said multi-echo MRI data is fitted to said single signal model using a model fitting algorithm. Said model fitting algorithm may be an instance of least squares estimation, iteratively reweighted least squares, least trimmed squares, or other robust approaches using m-estimators or s-estimators, any of which may be combined with zero, one or more regularisation terms.

In an example of the invention, the single signal model includes a spectral model of one of the at least two species with more than one spectral component.

Preferably, said single signal model includes at least one of the relaxation time quantities ($T_1$, $T_2$, $T_2^*$) to correct for signal decay.

In an embodiment of the invention, the starting condition values of the relaxation time quantities are in the physically observable range. Preferably, the starting condition values of the $T_2^*$ relaxation time quantities are between 1 to 100 ms. Further preferably, the starting condition values of the $T_2^*$ relaxation time quantities are between 20 to 30 ms at 1.5 tesla. Alternatively, for 3.0 tesla operation, the starting condition values of the $T_2^*$ relaxation time quantities are between 10 to 15 ms.

In an example of the invention, the method further comprises the step of using said species signal contribution to generate separate images showing the results for each species.

Preferably, one or more of the resulting images are post-processed.

In an example of the invention the separated species contributions are used to estimate a field heterogeneity ('fieldmap') term.

In a preferred embodiment of the invention the estimated relaxation quantities are used to estimate a field heterogeneity ('fieldmap') term.

Further preferably, the at least two species include at least two of water, fat, hyperpolarized contrast elements or metabolites of such elements, or markers for the presence of cancerous or malignant cells.

In an example of the invention, the method is applied on acquired MRI data of a phantom model.

In an example of the invention, the method is applied on acquired MRI data of human tissue including tissue from at least one of liver, pancreas, kidney, spleen, heart, muscle or adipose tissue.

In an example of the invention, cost function values in a certain voxel are used to update a likelihood map of the presence of at least one species in the voxel In accordance with another aspect of the invention there is also provided an image processing system arranged to analyse the magnitude of Magnetic Resonance Imaging (MRI) data from acquired MRI images of a subject, to determine the relative signal contributions of at least two species to each voxel of the images, the image processing system comprising at least one processing device arranged to: use the magnitude of the multi-echo MRI data of images from the subject, where the images are acquired at arbitrarily timed echoes including at least one echo time where water and fat are not substantially in-phase with each other; fit the magnitude of said multi-echo MRI data to a single signal model to produce a plurality of potential solutions for the relative signal contributions for each of the at least two species from the model, by using a plurality of different starting conditions to generate a particular cost function value for each of the plurality of starting conditions, where said cost function values are independent of a field map term for the MRI data; and analyse said cost function values to calculate the relative signal separation contribution for each species at each voxel of the images.

In accordance with an aspect of the invention, a non-transitory computer program product is provided. The non-transitory computer program product has executable program code stored therein, the program code operable for analysing the magnitude of MRI data in accordance with any of the methods described above.

The non-transitory computer program product comprises at least one from a group including: a hard disk, a CD-ROM, an optical storage device, a magnetic storage device, a Read Only Memory, ROM, a Programmable Read Only Memory, PROM, an Erasable Programmable Read Only Memory, EPROM, an Electrically Erasable Programmable Read Only Memory, EEPROM, and a Flash memory.

An example of this invention relates to a species separation method based only on the magnitude of multi-echo signals, that uses magnitude data only, and does not require any phase information. The method uses a biologically accurate signal model, and it embodies a multi-point search optimisation. The model of the invention is able to resolve the dominant species over the full dynamic fraction range (0%-100%), and it does not require the use of in-phase echoes, or more than one signal model nor any prior information about the body being imaged.

Existing methods (as described in the introduction) first estimate $B_0(x)$, then $w(x)$. By contrast, the method of this invention can estimate $w(x)$ directly, thus overcoming the problems with existing methods discussed in the introduction.

In a preferred embodiment of the invention only magnitude images are used, the estimates of the species (in a preferred example of the invention the species are fat and water) do not rely on initially estimating a fieldmap. As a result, the estimates of fat and water will be essentially invariant to uncertainties or inaccuracies resulting from any fieldmap estimation process. Furthermore, phase images are not needed to achieve fat-fraction estimates within the full dynamic range. Those versed in the art may note however that a fieldmap may later be estimated in order to improve the signal-to-noise ratio of the images obtained when fitting the magnitude of the MRI data. The method described below enables a user to choose an arbitrary combination of echo times and echo spacing, including at least one echo time where water and fat are not substantially in-phase with each other. That is, the method of this invention it is not limited to a particular set of echoes. As described, the main species of interest are fat and water, but the invention may also be used for other species including silicone, hyperpolarised contrast elements such as carbon-13, xenon-19 and helium-3, metabolites of such hyperpolarized contrast elements and also organic materials that may be indicators of tumours, cancers or other malignant materials including for example pyruvate and lactate.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
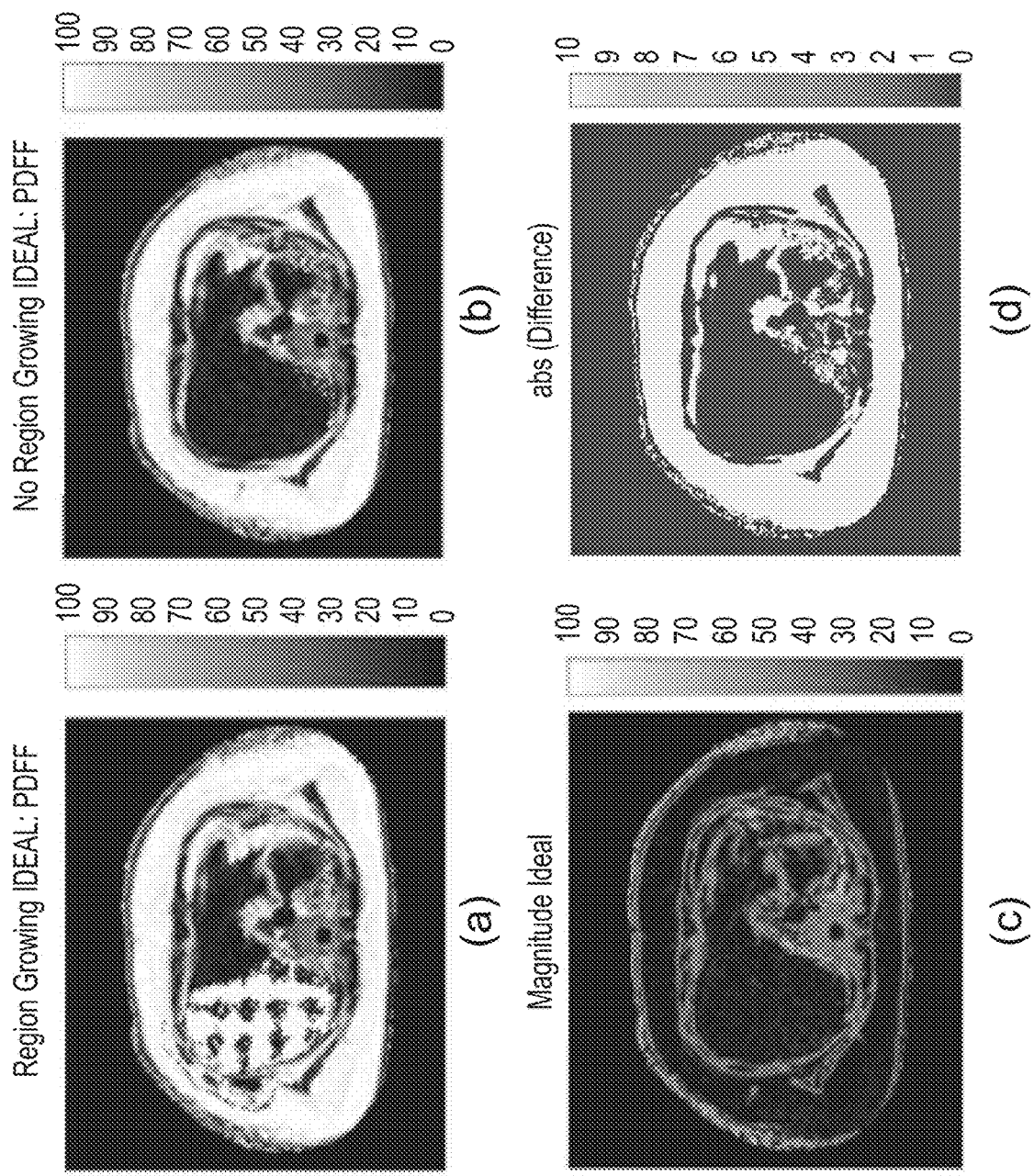
FIG. 1 illustrates MRI PDFF images obtained using prior art techniques.

The present invention will now be described with reference to the accompanying drawings in which there is illustrated an example of a method and apparatus for analysing only the magnitude data from MRI images that are acquired at arbitrarily timed echoes including at least one echo time where water and fat are not substantially in-phase with each other. The phase information is not needed in this method. However, it will be appreciated that the present invention is not limited to the specific examples herein described and as illustrated in the accompanying drawings.

Furthermore, because the illustrated embodiments of the present invention may for the most part, be implemented using electronic components and circuits known to those skilled in the art, details will not be explained in any greater detail than that considered necessary as illustrated below, for the understanding and appreciation of the underlying concepts of the present invention and in order not to obfuscate or distract from the teachings of the present invention.

As discussed above, most methods for species separation (where the species are preferably water and fat) in MRI images are based on complex data, that is, they rely on the availability of both magnitude and phase data in order to estimate the fieldmap, which is then used to estimate water and fat components of the image.

A magnetic resonance signal $s_i$ at a single voxel containing water, fat and iron (or other species) may be sampled at multiple echo times $t_i$ during relaxation. For a general complex-valued signal, the following phase-constraint model has been proposed:

$$s_i = (\rho_W + \rho_F \cdot \Sigma_p \alpha_p e^{j2\pi f_p t_i}) \cdot e^{j(2\pi \psi t_i + \phi_0)} \cdot e^{-R_2^* t_i} + n_i \quad \text{Equation 1}$$

where $\rho_W$ and $\rho_F$ are the unknown water and fat quantities, respectively, and $R_2^* = 1/T_2^*$ (s$^{-1}$) is an unknown relaxation quantity. $\rho_W$ and $\rho_F$ are real-valued variables that have associated phase terms $e^{j\phi_W}$ and $e^{j\phi_F}$, where $\phi_W = \phi_0$ may be assumed.

In the above equation $s_i$ is actually $s_i(x)$, and $\rho_w$ is $\rho_w(x)$, but explicit mention of the spatial parameter (x) clutters the equation, and so established practice is that x is supressed in the equation.

The field map $\psi$ is modelled as a phase shift. The signal is further affected by noise ($n_i$) which is typically ignored in subsequent derivations, implicitly assuming high enough signal-to-noise ratio (SNR) acquisitions. PDFF may be calculated from the water and fat amounts using $$PDFF = \frac{\rho_F}{\rho_W + \rho_F} \times 100.$$

The term $\Sigma_p \alpha_p e^{j2\pi f_p t_i}$ is the multi-peak fat spectral model with P peaks: $\alpha_p$ is the amplitude of the fat peak p relative to the amplitude of the water peak, and $f_p$ is the difference in precession frequency of the fat peak p with respect to the water peak in Hz (16, 38). It is usual practice to assume that the values $\{\alpha_p, f_p\}$ for all p are known empirically and constant throughout the image.

The alleged inability of magnitude-based water-fat separation methods to determine PDFF values above 50% is known as the 'fat-water ambiguity' challenge, and may be explained mathematically (Bydder et al., 2008; Yu et al., 2011). With magnitude-based methods, Equation 1 above in which |a| refers to the magnitude of a, has to be optimised for a given set of echo signals $s_i$, $$|s_i| = |(\rho_W + \rho_F \cdot \Sigma_p \alpha_p e^{j2\pi f_p t_i}) \cdot e^{-R_2^* t_i}|. \quad \text{(Equation 1a)}$$

As expected, the phase term vanishes, as does the field map parameter.

Note that there is a set of equations for each and every voxel in an MRI image, and the goal is to estimate the fat-water fraction $$PDFF = \frac{\rho_F}{\rho_W + \rho_F} \times 100$$

fraction (given as a %) for each voxel in the image. In the magnitude only formulation of the problem, there is no fieldmap term (that is familiar from complex variations), since $B_0$ inhomogeneity is generally modelled (at each voxel) as a constant phase shift.

To illustrate the fundamental problem, we assume for the moment that fat is modelled as having a spectrum with a single-peak (p=1), so that $\Sigma_p \alpha_p e^{j2\pi f_p t_i}$ becomes $e^{j2\pi \Delta f t_i}$, whose magnitude $|e^{j2\pi \Delta f t_i}| = 1$. Equation 1 now becomes $$|s_i| = |(\rho_W + \rho_F) \cdot e^{-R_2^* t_i}|. \quad \text{(Equation 2)}$$

The fat-water ambiguity that is reportedly inherent to magnitude-based methods is immediately evident in Equation 2 in that exchanging $\rho_W$ and $\rho_F$ does not change the value of the equation (Yu et al., 2011). Both solutions are equally valid even though in reality there will only be one "true" solution $\{\rho_W, \rho_F\}_t$, the other being an aliased solution $\{\rho_W, \rho_F\}_a$.

The two solutions are simply related, since $PDFF_a = 100\% - PDFF_t$ holds. Note that $R_2^*$ will be equal for both solutions. We may simulate the optimisation space for:

a given field strength (1.5 T); an arbitrary set of echoes ({1.2, 3.2, 5.2, 7.2, 9.2, 11.2} ms); and true values {PDFF, $R_2^*\}_t=\{75\%, 45\ s^{-1}\}$. This field strength is chosen as the strength of a generally available MRI scanner, with 3 T considered a "high field". By generating a true noise-free signal $s_i|\{PDFF, R_2^*\}_t$ and then comparing the true signal with a signal generated at each possible $\{PDFF, R_2^*\}$ point in space, a continuous map of 'cost function values' is produced.

Figure 2:
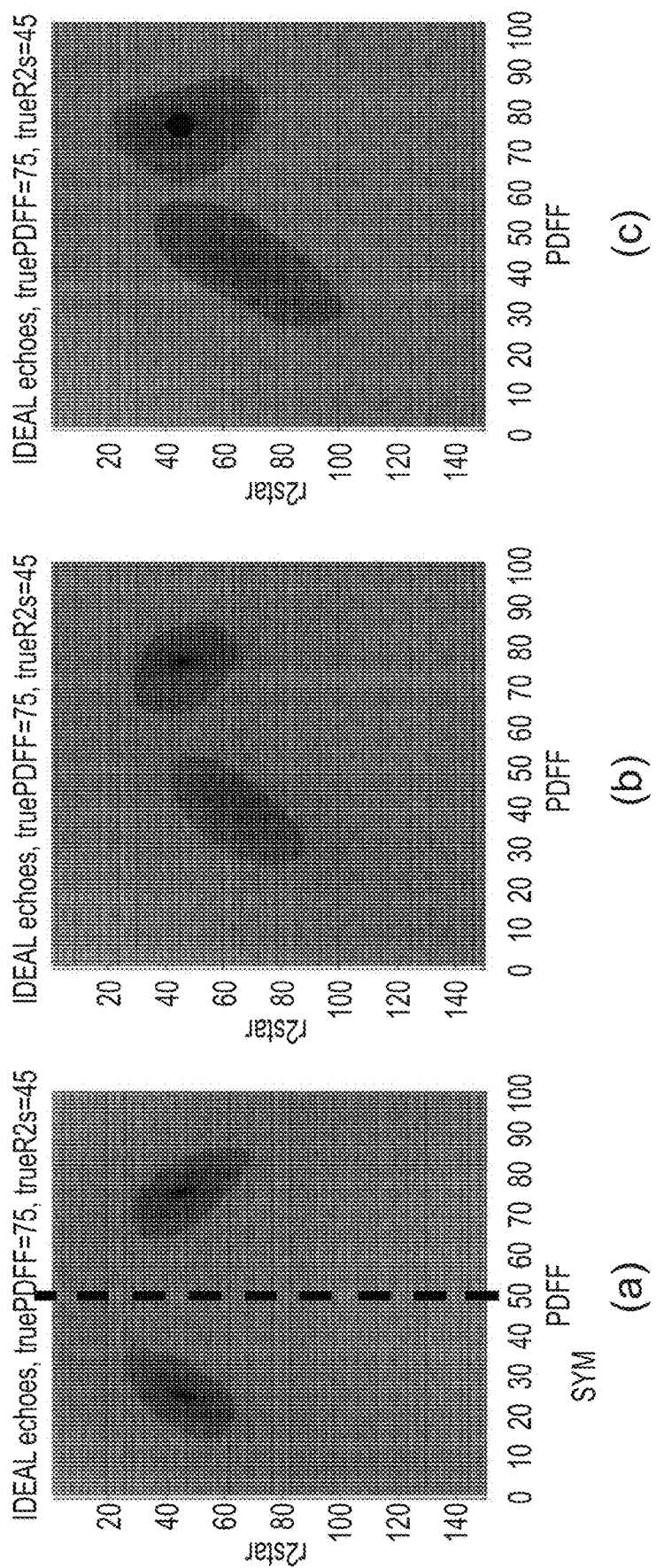
FIG. 2 shows example cost function value maps.

FIG. 2 shows examples of cost function value maps obtained under different conditions, when the optimisation space is reduced to two dimensions ($\rho_W$ and $\rho_F$ may be combined into PDFF for dimensionality reduction to allow visualisation; and $R^*_2$) when using magnitude-based estimation. FIG. 2(a) shows the simplest case where the fat is modelled as a single-peak spectrum. In this case there is unresolvable fat-water ambiguity, reflected as symmetry in the optimisation space. FIG. 2(b) is the result when fat is modelled as a multi-peak spectrum. As seen in this image, ambiguity still exists and is reflected as a local minimum but there is no longer symmetry about PDFF=50% in the image. The ambiguity in FIG. 2(b) may be resolvable using the multi-point search optimisation of this invention, with different initial conditions, where the dot in the top right-hand quadrant of the image of FIG. 2(c) indicates the chosen solution.

When the spectrum of fat is assumed to consist of a single peak, there will be two minima, $\{\rho_W, \rho_F\}_t$ and $\{\rho_W, \rho_F\}_a$, and the unresolvable ambiguity will be reflected by a symmetrical optimisation space as shown in FIG. 2(a) The choice of which of these two local minima is found by an optimisation algorithm will be determined by and is sensitive to the initial condition. Specifically, if, as is almost always the case in previously reported methods, the algorithm is initialised near to PDFF=0% then it will always converge to values below 50%.

Figure 3:
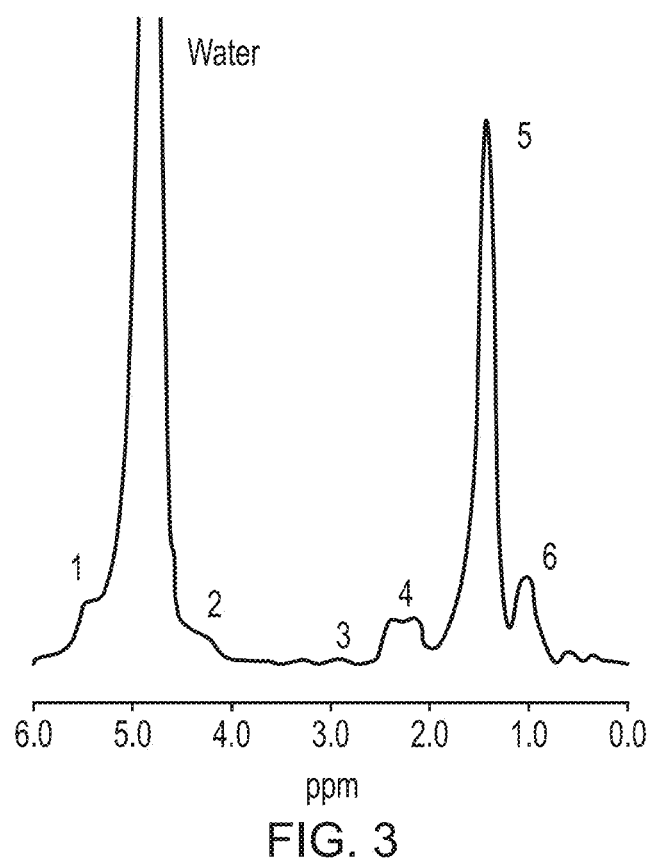
FIG. 3 is a frequency spectrum for fat.

Now suppose that fat is modelled more realistically as having a multi-peak spectrum, as shown in FIG. 3, for example (p=6; Hamilton et al., 2011), then in Equation 1, $|\Sigma_p\alpha_p e^{i2\pi f_p t_i}|$ will no longer be equal to 1, and exchanging $\rho_W$ and $\rho_F$ will change the value of the equation 2 (Yu et al., 2011). In the optimisation space, the 'swapped' solution $\{\rho_W, \rho_F\}_a$ now appears as a local minimum, where $PDFF_a \neq 100\%-PDFF_t$; the converged $R_2^*$ will now be different in both solutions (as shown in FIG. 2(b). Note that in this multi-peak situation, an optimisation algorithm initialised near PDFF=0% will still converge to values below 50%. Conversely, the same optimisation algorithm initialised near PDFF=100% will converge to the local solution greater than 50%. This ambiguity now is resolved by comparing the cost function values at both minima—achieved with at least two different sets of initial conditions—and choosing the solution with the lowest cost function value (FIG. 2(c)).

Figure 4:
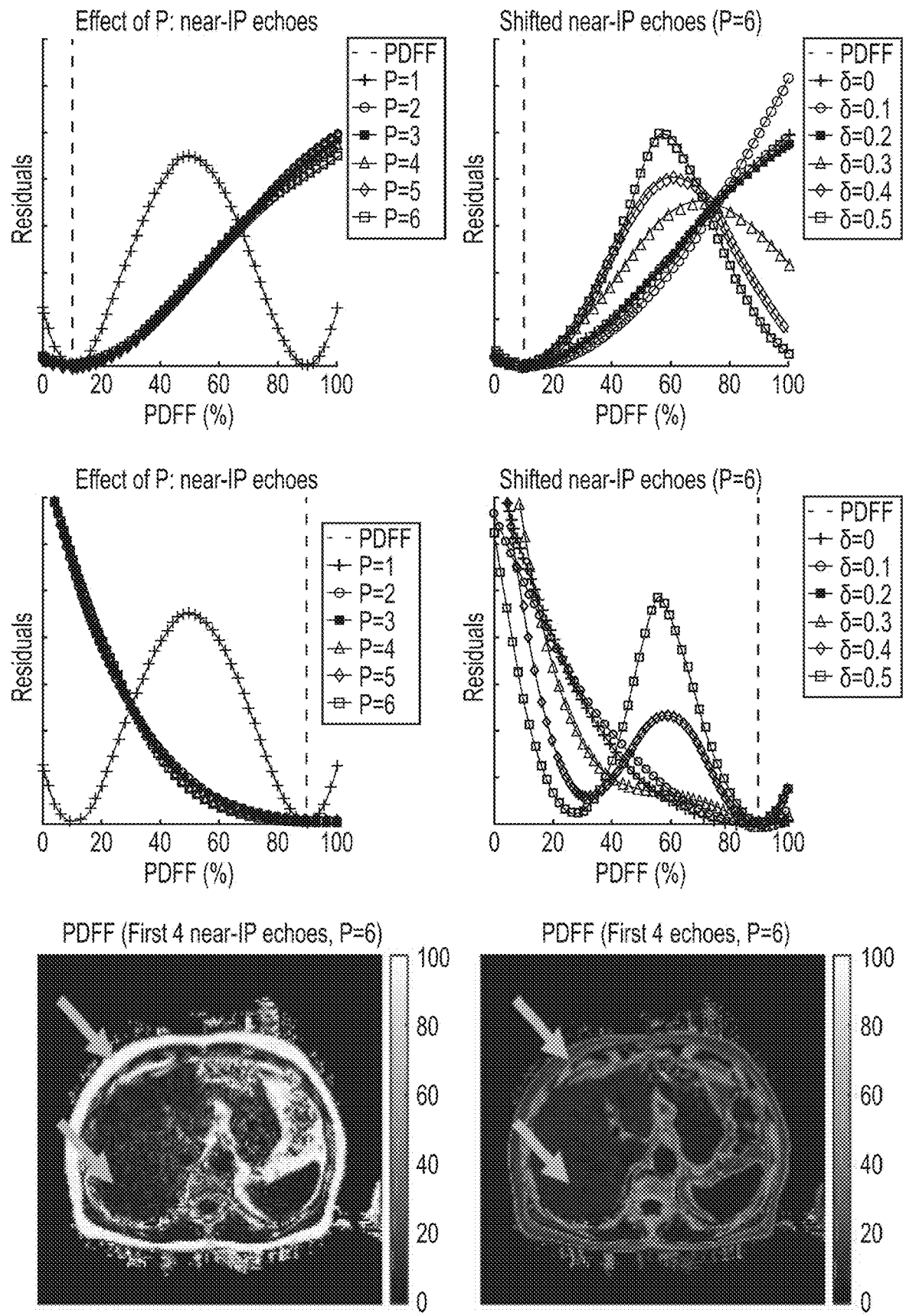
FIG. 4 illustrates magnitude related water fat ambiguity using spectral peaks and echo shifts.

In an example of the invention we use a multi-peak spectral model, preferably the spectrum is for fat, with P=6, as this is the value most commonly used in the literature, however spectral model(s) for at least one of the two species may be used as long as the model has more than one spectral component. We may now move away from the in-phase acquisition by shifting the echo sampling by a known shift $\delta$, so that $t_i=(i-\delta)/\Delta f$; $\delta=0.5$ thus meaning an opposed-phase acquisition. This is illustrated with reference to FIG. 4. The left-hand column of this figure is results for using in-phase echoes with variable amount of P, whereas the righthand column is for results using variable arbitrarily timed echoes, and P=6 in accordance with an example of this invention.

Figure 5:
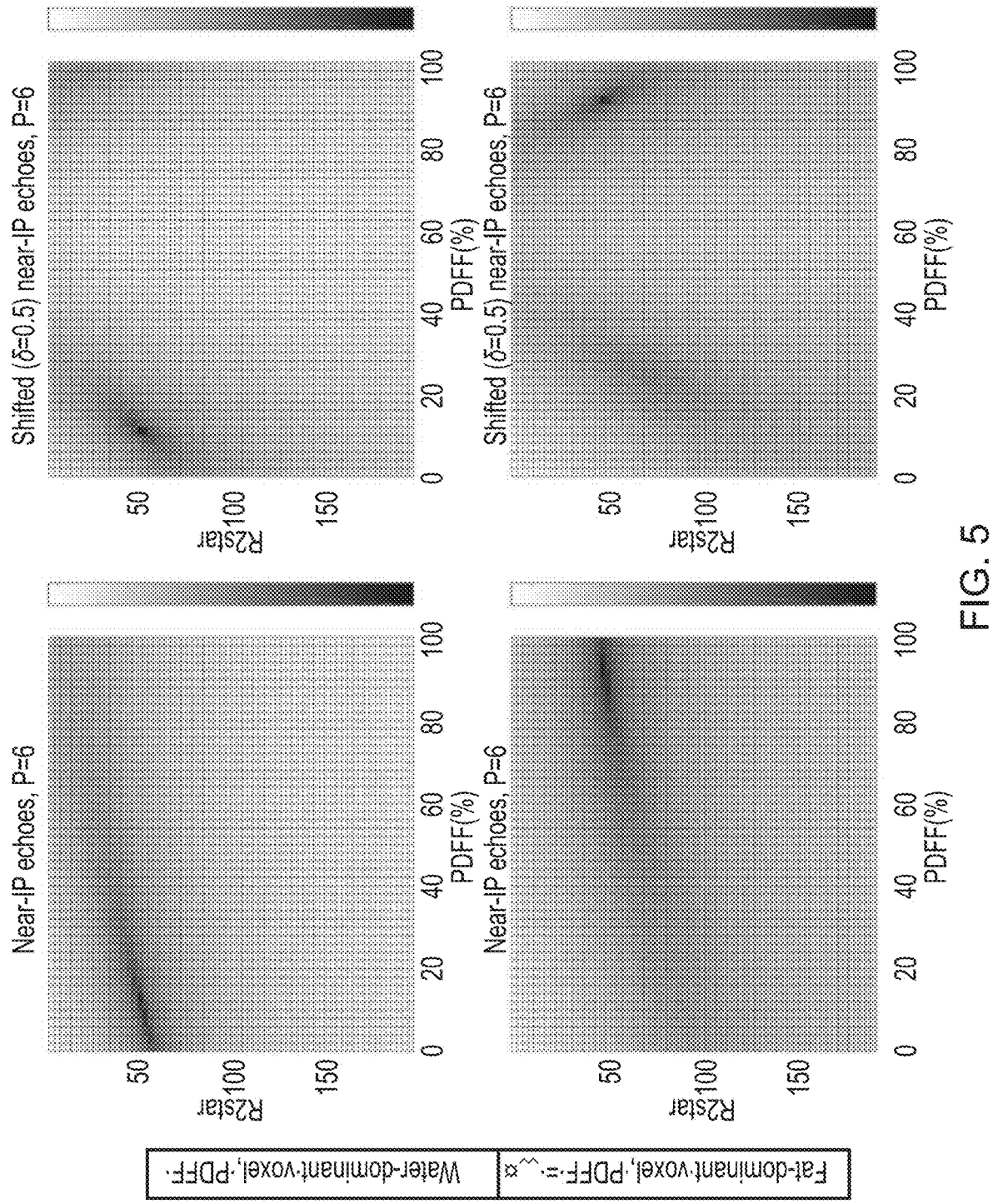
FIG. 5 illustrates example cost function value maps as used in an example of the invention.
Figure 6:
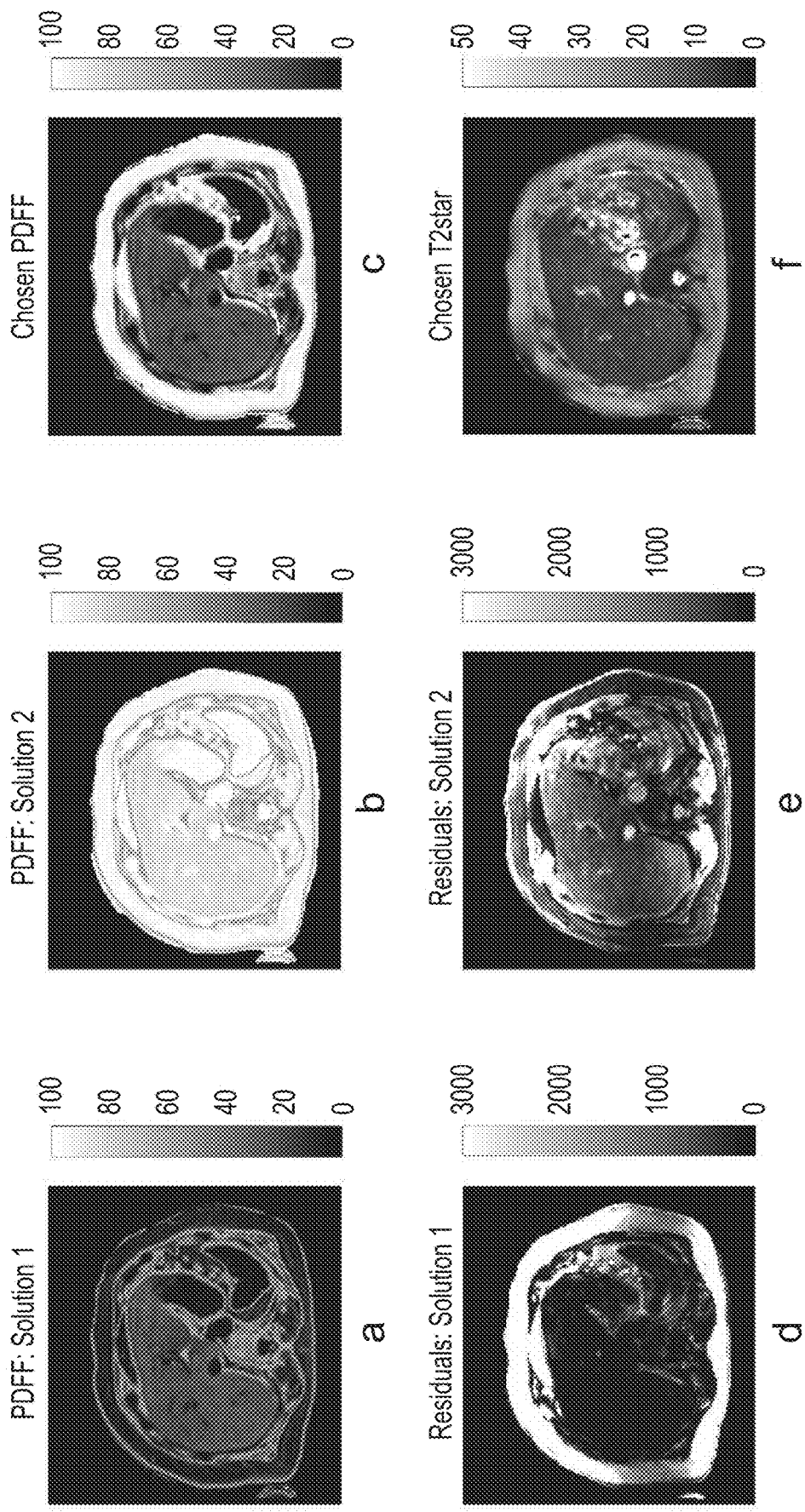
FIG. 6 illustrates example MRI PDFF images obtained using the method of the invention.

That is, the magnitude only of the multi-echo MRI data is used, with MRI images acquired at arbitrarily timed echoes including at least one echo time where water and fat are not substantially in-phase with each other. The top row shows graphs for a water dominant voxel (PDFF 10%), the central row shows the results for a fat dominant voxel (PDFF 90%). While PDFF may be resolved in the 0-100% range for substantial $\delta$, a local minimum appears for increasing $\delta$; in general, for an asymmetric combination of echo times, there are two local minima for the physical range of PDFF and $R_2^*$ (FIG. 6 graphs in right hand column). Note that optimisation algorithms initialised near 0% PDFF will converge to the correct solution for water-dominant voxels (FIG. 5 top and bottom images on right hand side), but they will converge to the local minimum for fat-dominant voxels (FIG. 5 $2^{nd}$ and bottom images on right hand side). Magnitude-based estimation methods previously described in the literature have consistently exhibited this behaviour, with true PDFF>50% values aliased to solutions below 50%. it is understood that the method disclosed here works so long as P>1. If 1<P<6 then the minimum we seek is less pronounced. If P>6 the extra spectral peaks, which are very low (e.g. give height of the 6th peak relative to the first one) then there is little or no additional benefit since the MRI data is discrete, relatively coarsely sampled, and subject to noise.

The magnitude-related water-fat ambiguity may now be resolved because the solutions at the local minima will now have higher cost function values than the true solutions, using the presented magnitude multi-peak model. We present a multipoint method that aims to explore both possible solutions and resolve the magnitude-related water-fat ambiguity for arbitrarily timed echoes including at least one echo time where water and fat are not substantially in-phase with each other.

In summary, the classical magnitude-based related fat-water ambiguity challenge may be resolvable by using:
magnitude data only, to reduce the possible minima from many (using the complex-based approach that requires both magnitude and phase; see ref 24) to only two potential minima;
multi-peak fat spectrum modelling, to break the symmetry and thus making the two possible minima distinguishable; and
an optimisation technique that ensures both minima are explored, to compare the cost function values at both solutions and choose the solution associated with the lowest cost function value.

Our method has been applied to an example range of different clinical cases, and its accuracy, precision and robustness to artefacts (especially fat-water swaps) has been evaluated.

The accuracy of the magnitude-based method of this invention (MAGO) was tested in vivo against an in-house implementation of the prior art IDEAL method, for two different sets of data, where the in-house IDEAL (LMS IDEAL) method was considered the reference standard. LMS IDEAL has been previously validated against phantom data and a set of in vivo data.

In order to ensure that both possible solutions are explored, the initial values of water and fat quantities need to be combined to a low PDFF in at least one run of the algorithm and to a high PDFF in at least one other run. The initial value for the relaxation quantity $R_2^*$ may be set within the physiologically expected range in all runs. A given converged solution set ($\rho_W$, $\rho_F$, $R_2^*$) has an associated cost function value in the form of the expression cost function value $(\rho_W, \rho_F, R_2^*) = \Sigma_i^N(|\hat{s}_i| - |s_i|)^2$, where $\hat{s}_i$ is the estimated signal using the converged solution set $(\rho_W, \rho_F, R_2^*)$ in Equation 2.

Note that this definition of the cost function value is independent of a field map term. We choose as solution at each voxel the one with the lowest cost function value, though the other minima may be retained as alternative solutions.

An example of the magnitude-based method of this invention was implemented using the lsqcurvefit function in the Matlab program (The MathWorks, Inc.). Alternatively, the method may be performed using compiled C++ routines using ITK (www.itk.org). Nonlinear fitting of the data was performed twice, each time with a different set of initial conditions for the data. As discussed above, the data is the magnitude only of the multi-echo MRI data of images from the subject, where the images are acquired at arbitrarily timed echoes including at least one echo time where water and fat are not substantially in-phase with each other. In preferred embodiments of the invention all echoes may be used in a single step when performing the fitting of the magnitude data to the single signal model.

Preferably, the magnitude of the multi-echo MRI data is fitted to the single signal model using an estimation model. In a preferred example of the invention, this uses one or more of the following: regularised least squares estimation; iteratively weighted least squared estimation, m-estimators or s-estimators. Alternatively, other estimation models may be used for fitting the MRI data to the single signal model.

The complex-valued vector $\Sigma_p \alpha_p e^{j2\pi f_p t_i}$ was calculated a priori and the value was used for all voxels and during optimisation. The three unknown parameters $\rho_W$, $\rho_F$ and $R_2^*$ were estimated from two different sets of initial values. Both first estimates of the signal relaxation parameter were set within the physiologically meaningful range to $R_2^* = 50$ s$^{-1}$. In an example of the invention, at least one of the relaxation time quantities, $T_n^*$, is used to correct for signal decay, and is preferably in the physically observable range between 1 to 100 ms, still further preferably it is between 20 and 30 ms, when the operational field strength is 1.5 tesla. Alternatively, for a field strength of 3 tesla, the time quantities may be between 10 to 15 ms. If PDFF and R2* are not estimated simultaneously (as they are in the known IDEAL methods), then the PDFF may be inaccurate as it does not correct for $R_2^*$ decay, and also $R_2^*$ may be inaccurate as it does not correct for the presence of fat. Furthermore, PDFF and $R_2^*$ may be less robust and dependent on acquisition parameters, e.g. the chosen number of echoes. Previous studies (31) have shown this effect using simulations and in vivo data.

Initial estimates of water and fat amounts were as follows: $\{\rho_W, \rho_F\}_1 = \{1000, 0\}$ in the first run and the opposite in the second run, $\{\rho_W, \rho_F\}_2 = \{0, 1000\}$, so PDFF$_1$=0% and PDFF$_2$=100%. The scaling of these initial conditions was chosen empirically to account for different scanner gains across acquisition settings. For each run, two sets of solutions $\{\rho_W, \rho_F, R_2^*\}$ were obtained at each voxel as shown in FIG. 6.

The first and second converged solutions had two associated cost function values. Cost function values were in the form of the expression cost function value $(\rho_W, \rho_F, R_2^*) = \Sigma_i^N(|\hat{s}_i| - |s_i|)^2$, where $\hat{s}_i$ was the estimated signal using a solution set $(\rho_W, \rho_F, R_2^*)$ in Equation 2. Note the definition of the cost function values is also independent of a field map term. The solution set with lowest cost function value was chosen as the "correct" solution at each voxel, whereas the other solution was kept as the alternative solution, and $T_2^* = 1/R_2^*$ maps were calculated.

From the first step, two converged data sets were obtained, where it is presumed that one of the data sets was the true solution. Each of the two solutions had an associated squared 2-norm of the cost function value. The final solution at each voxel was assigned based on those cost function values, where the converged set associated with the lowest cost function value was chosen. The alternative solution was stored. No additional conditions were imposed at this point, (though those versed in the art may imagine many techniques to correlate neighbouring voxels and further improve the fitting at the decision step), similarly to the fieldmap estimation problem.

FIG. 6 shows intermediate and final results of an example of the magnitude only implementation of this invention on a typical case (from Uniklinik Ulm). In each case, the method uses the magnitude of the multi-echo MRI data of images from the subject, where the images are acquired at arbitrarily timed echoes including at least one echo time where water and fat are not substantially in-phase with each other.

The first PDFF map (FIG. 6 a) relates to the first converged solution at each voxel independently and is evidently associated with the lower of the two possible PDFF minima in the general case of an acquisition with an arbitrary echo combination, including at least one echo time where water and fat are not substantially in-phase with each other. This first PDFF map shows the subcutaneous fat region containing PDFF values in the 0-20% range, while PDFF values within the liver are in the plausible range. Note the PDFF map from solution 1 alone is analogous to output PDFF maps from conventional magnitude-based methods. On the other hand, the second PDFF map (FIG. 6b) is associated with the higher of the two possible PDFF minima. This map shows unfeasibly high liver PDFF values, but the subcutaneous fat is estimated correctly. The cost function values for both solutions may be compared and used to choose the most likely correct solution at each voxel independently; this step allows resolving the magnitude-related water-fat ambiguity. It may be the case that two spatially separated voxels with similar PDFF values have substantially different absolute cost function values (see subcutaneous fat in FIG. 6d); it is the relative value of the cost function from solution 1 to solution 2 at the same location that is compared. For this particular acquisition, differences between cost function values may exceed an order of magnitude, so water-fat separation is highly robust and does not require any connectivity analysis. However, in some examples of the invention, the image may be processed, and connectivity analysis, or other analysis may be performed.

The method of this invention was first assessed using a publicly available dataset of twenty-eight phantom acquisitions (http://dx.doi.org/10.5281/zenodo.48266). A phantom comprising a total of eleven vials with peanut oil and water mixtures (PDFF: 0%, 2.6%, 5.3%, 7.9%, 10.5%, 15.7%, 20.9%, 31.2%, 41.3%, 51.4%, 100%) was scanned at different sites (Philips, Siemens and GE Healthcare) using two different six-echo gradient echo protocols at 1.5 T and 3 T: Protocol 1 was a near in-phase/opposed-phase acquisition (TE$_1 \approx \Delta$TE$\approx$2.30 ms at 1.5 T and TE$_1 \approx \Delta$TE$\approx$1.00 ms at 3 T) and Protocol 2 aimed for the shortest possible echoes (TE$_1$=1.10-1.20 ms and $\Delta$TE$\approx$2.00 ms at 1.5 T, and $\Delta$TE$\approx$1.15 ms at 3 T). Acquisitions were designed with a small flip angle (2°-3°) to minimise $T_1$ bias and combined monopolar and bipolar readouts.

Complex-valued data were available for all acquisitions, but in order to assess the magnitude only method of this invention, the phase information was discarded. The signal model used a six-peak peanut oil fat spectrum corrected for room temperature effects (22° C., relative frequencies in ppm [0.50 −0.49 −2.04 −2.70 −3.50–3.90], relative amplitudes [0.048 0.039 0.004 0.128 0.694 0.087]). 15 mm diameter ROIs were placed manually and were used to extract a median value for each phantom vial from the central slice. Median MRI-PDFF values were plotted against designed phantom concentrations and linear regression was performed for comparison to the available IDEAL results.

Figure 7:
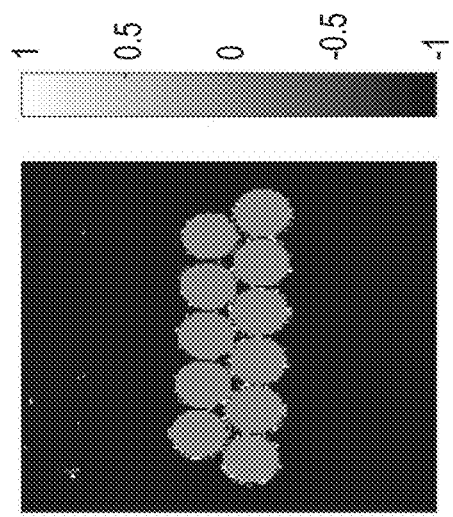
FIG. 7 shows MRI PDFF images obtained using the method of the invention.
Figure 7:
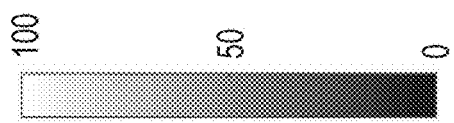
Figure 7:
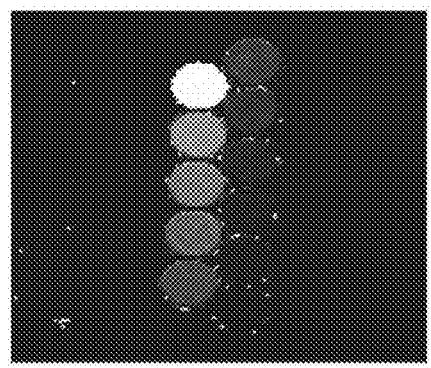
Figure 7:
Figure 7:
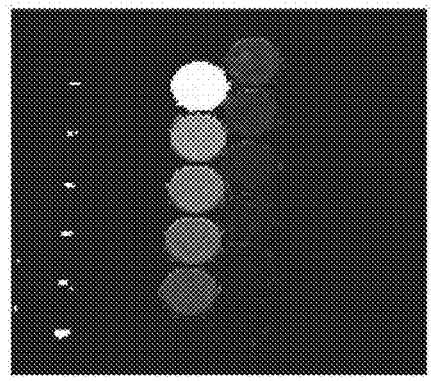

FIG. 7 shows the extracted median PDFF values from the ROIs placed on all 11 phantom vials, for all sites, acquisition protocols and field strengths. FIG. 7(a) is the PDFF result according to the prior art method of Hernando, image (b) is using the method of this invention, and image (c) is the difference between the images. Both Protocol 1 and Protocol 2 in the phantom acquisitions used at least one echo time where water and fat were not substantially in-phase with each other: in Protocol 1, these would be any of the opposed-phase echoes; in Protocol 2, these would be most echoes present, as the echoes were not timed according to water and fat resonance frequency shifts.

Figure 8:
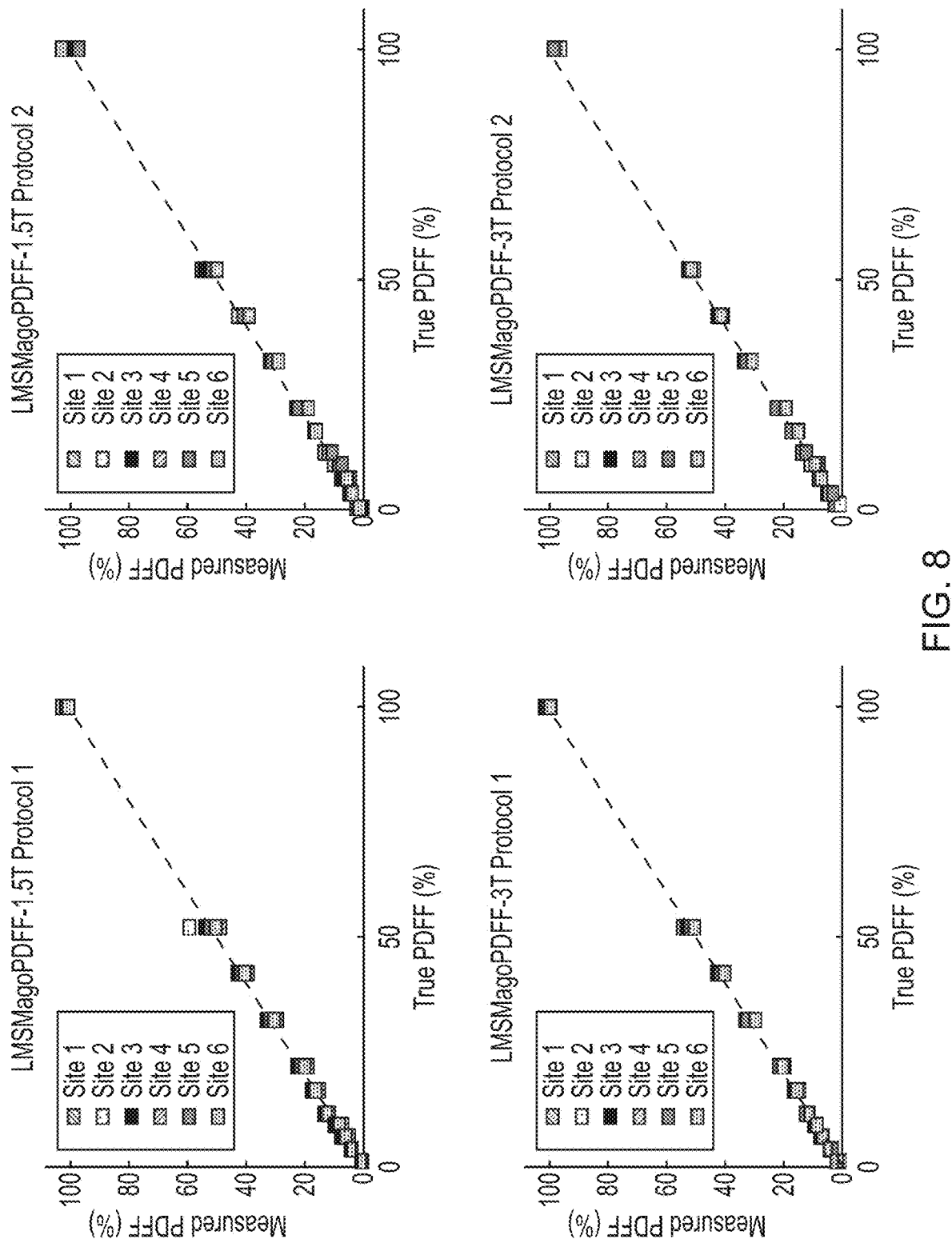
FIG. 8 show the relationship between measured and true PDFF for images obtained under different conditions.

Linear regression results are shown qualitatively in FIG. 8 and quantitatively in Table 1 in terms of slope, intercept, and R-squared agreement between ground truth values and designed phantom concentrations.

acquisition is shown in FIG. 7 $a$, with PDFF maps obtained from existing methods and also calculated with the method of this invention, reporting excellent voxel-wise agreement between methods (note the −1 to 1% scaling), and similar noise performance, even though MAGO used half the available information (magnitude data only). Table 1 compares results from the downloaded PDFF maps against the calculated ones and reports both excellent agreement between both methods in-vitro and high accuracy (note high R-squared coefficients, slope close to 1 and intercept close to 0). This encourages the feasibility of the MAGO method for six-echo acquisition protocols.

In this example of the invention the method is able to resolve the magnitude-related water-fat ambiguity after PDFF=50% in all cases, mainly reflected in the 100% phantom vial results, and without compromising accuracy over the 0-50% PDFF range. In general, higher agreement between methods and between MAGO and ground truth values was reported on Protocol 2 data over Protocol 1 data, and also on 3 T data over 1.5 T data.

Research Subjects

In an example of the method of the invention two different sets of test data were used for in vivo testing, each of the test sets having a different purpose. The first test set was a validation set, with more controlled, reliable magnitude and

TABLE 1

| Site | MAGO PDFF 1.5T Protocol 1 | | | Hernando PDFF 1.5T Protocol 1 | | |
|---|---|---|---|---|---|---|
| | $R^2$ | Slope [95% CI] | Intercept [95% CI] | $R^2$ | [Slope [95% CI] | Intercept [95% CI] |
| 1 | 0.999 | 1.00 [0.97 1.03] | 0.41 [−0.67 1.48] | 0.999 | 1.00 [0.97 1.02] | 0.42 [−0.66 1.50] |
| 2 | 0.997 | 1.04 [0.99 1.08] | 0.81 [−0.93 2.55] | 1 | 1.02 [1.00 1.03] | 0.73 [0.15 1.32] |
| 3 | 0.999 | 1.01 [0.99 1.03] | 0.31 [−0.52 1.14] | 0.999 | 1.01 [0.99 1.04] | 0.33 [−0.55 1.22] |
| 4 | 0.997 | 0.99 [0.95 1.04] | −0.57 [−2.27 1.13] | 0.997 | 0.99 [0.95 1.04] | −0.55 [−2.24 1.14] |
| 5 | 0.999 | 1.00 [0.99 1.02] | 0.18 [−0.50 0.87] | 0.999 | 1.01 [0.99 1.02] | 0.21 [−0.46 0.88] |
| 6 | 0.998 | 1.00 [0.96 1.03] | −0.15 [−1.37 1.06] | 0.998 | 1.00 [0.96 1.03] | −0.14 [−1.34 1.07] |

| Site | MAGO PDFF 1.5T Protocol 2 | | | Hernando PDFF 1.5T Protocol 2 | | |
|---|---|---|---|---|---|---|
| | $R^2$ | Slope [95% CI] | Intercept [95% CI] | $R^2$ | [Slope [95% CI] | Intercept [95% CI] |
| 1 | 0.998 | 1.02 [0.99 1.06] | 0.08 [−1.25 1.40] | 0.998 | 1.02 [0.99 1.06] | 0.09 [−1.21 1.39] |
| 2 | 0.999 | 1.02 [1.00 1.04] | 0.99 [0.28 1.71] | 0.999 | 1.02 [1.00 1.04] | 1.01 [0.29 1.74] |
| 3 | 0.998 | 1.01 [0.97 1.04] | −0.38 [−1.58 0.82] | 0.999 | 1.00 [0.98 1.03] | 0.39 [−1.46 0.68] |
| 4 | 0.998 | 0.97 [0.94 1.00] | 0.08 [−1.06 1.21] | 0.998 | 0.97 [0.94 1.00] | 0.09 [−1.04 1.21] |
| 5 | 1 | 0.96 [0.95 0.98] | 1.26 [0.68 1.84] | 1 | 0.98 [0.96 0.99] | 1.08 [0.67 1.50] |
| 6 | 0.995 | 1.01 [0.96 1.06] | −0.74 [−2.72 1.25] | 0.995 | 1.01 [0.96 1.06] | −0.71 [−2.69 1.26] |

| Site | MAGO PDFF 3T Protocol 1 | | | Hernando PDFF 3T Protocol 1 | | |
|---|---|---|---|---|---|---|
| | $R^2$ | Slope [95% CI] | Intercept [95% CI] | $R^2$ | [Slope [95% CI] | Intercept [95% CI] |
| 1 | 0.998 | 1.00 [0.97 1.03] | −0.03 [−1.20 1.14] | 0.998 | 1.00 [0.97 1.03] | 0.01 [−1.17 1.15] |
| 2 | 0.999 | 1.01 [0.99 1.03] | 0.83 [0.11 1.55] | 0.999 | 1.01 [0.99 1.03] | 0.85 [0.12 1.58] |
| 3 | 0.999 | 1.01 [0.99 1.03] | 0.36 [−0.40 1.11] | 0.999 | 1.01 [0.99 1.03] | 0.38 [−0.38 1.13] |
| 4 | 0.997 | 1.00 [0.96 1.04] | −0.13 [−1.71 1.44] | 0.997 | 1.00 [0.96 1.04] | −0.12 [−1.68 1.45] |
| 5 | 0.999 | 1.00 [0.98 1.01] | 0.56 [−0.14 1.26] | 0.999 | 1.00 [0.98 1.01] | 0.57 [−0.12 1.26] |
| 6 | 0.998 | 0.99 [0.96 1.02] | −0.45 [−1.74 0.84] | 0.998 | 0.99 [0.96 1.02] | −0.43 [−1.71 0.85] |

| Site | MAGO PDFF 3T Protocol 2 | | | Hernando PDFF 3T Protocol 2 | | |
|---|---|---|---|---|---|---|
| | $R^2$ | Slope [95% CI] | Intercept [95% CI] | $R^2$ | [Slope [95% CI] | Intercept [95% CI] |
| 1 | 0.999 | 0.98 [0.96 1.00] | 0.39 [−0.36 1.15] | 0.999 | 0.98 [0.96 1.00] | 0.40 [−0.34 1.15] |
| 2 | 1 | 0.98 [0.97 0.99] | 0.42 [−0.12 0.96] | 1 | 0.98 [0.97 0.99] | 0.43 [−0.11 0.97] |
| 3 | 0.999 | 0.97 [0.95 1.00] | 1.18 [0.12 2.24] | 0.999 | 0.97 [0.95 1.00] | 1.18 [0.15 2.21] |
| 4 | 0.999 | 0.96 [0.94 0.99] | 0.84 [−0.13 1.81] | 0.999 | 0.96 [0.94 0.99] | 0.84 [−0.13 1.82] |
| 5 | 0.999 | 0.98 [0.96 1.00] | 0.69 [−0.15 1.53] | 0.999 | 0.98 [0.96 1.01] | 0.61 [−0.25 1.48] |
| 6 | 0.998 | 0.97 [0.94 1.00] | 0.20 [−1.01 1.41] | 0.998 | 0.97 [0.94 1.00] | 0.20 [−1.00 1.41] |

Linear regression was performed distinguishing between field strengths (1.5 T and 3 T) and protocols (Protocol 1 and Protocol 2) and averaging across sites. A representative phase data from healthy volunteers to assess the accuracy of the new method against a standard, the complex-based LMS IDEAL, which served as the reference method. The second test set explored the robustness of the two methods to a breadth of realistic acquisition conditions, which may output less reliable data and lead to the presence of artefacts.

An initial test set used in an example of the invention, consisted of single-slice protocol acquisitions from UK Biobank, using a Siemens 1.5 T MAGNETOM Aera, and consisted of N=186 nominally healthy volunteers, with expected low iron and low fat content values. The mentioned protocol had 6 echoes, with echo times={1.2, 3.2, 5.2, 7.2, 9.2, 11.2} ms. 8 cases were discarded due to not having an automatic segmentation mask (which will become relevant in data analysis).

Figure 9:
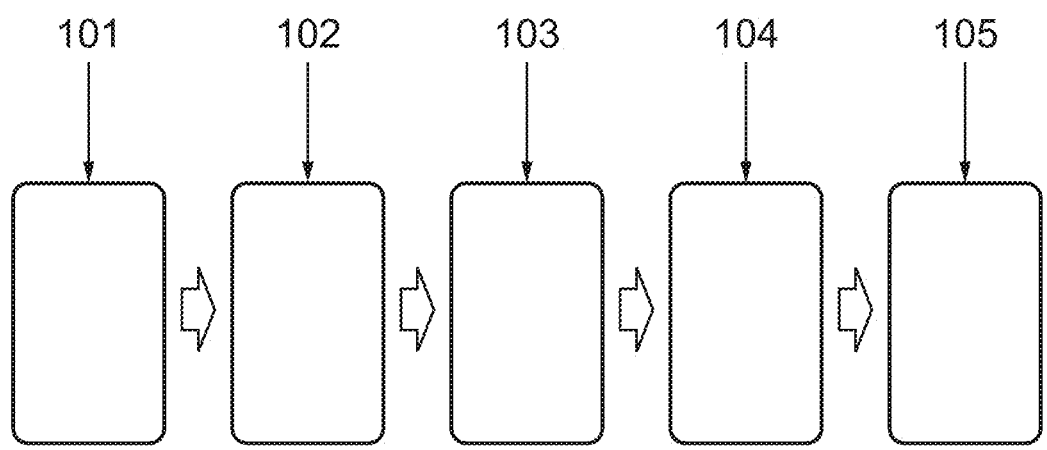
FIG. 9 is a flow chart showing the steps involved in the method of this invention.

FIG. 9 shows the data analysis pipeline as carried out for the test set. At 101 the magnitude-based algorithm implementation was applied to each case in each data set. At 102 liver segmentation masks were used to draw a median value of PDFF/$T_2$* within the liver. This is similar to how data analysts draw median values from manually placed ROIs. Reported values were compared to the reference processing method to assess bias and precision of the magnitude-based method (Bland-Altman plot). Then, at 103 automatic liver segmentation masks were used to draw PDFF and T2* histogram-type distributions within the liver mask. In a similar way to how PDFF/T2* values are reported by data analysts (median value of 3 manually placed ROIs), the median values of both PDFF and T2* distributions were reported at 104. Those values were then compared at 105 with the references from LMS IDEAL, also median values drawn from the same liver segmentation.

Results

Validation (Biobank Test Set)

Figure 10:
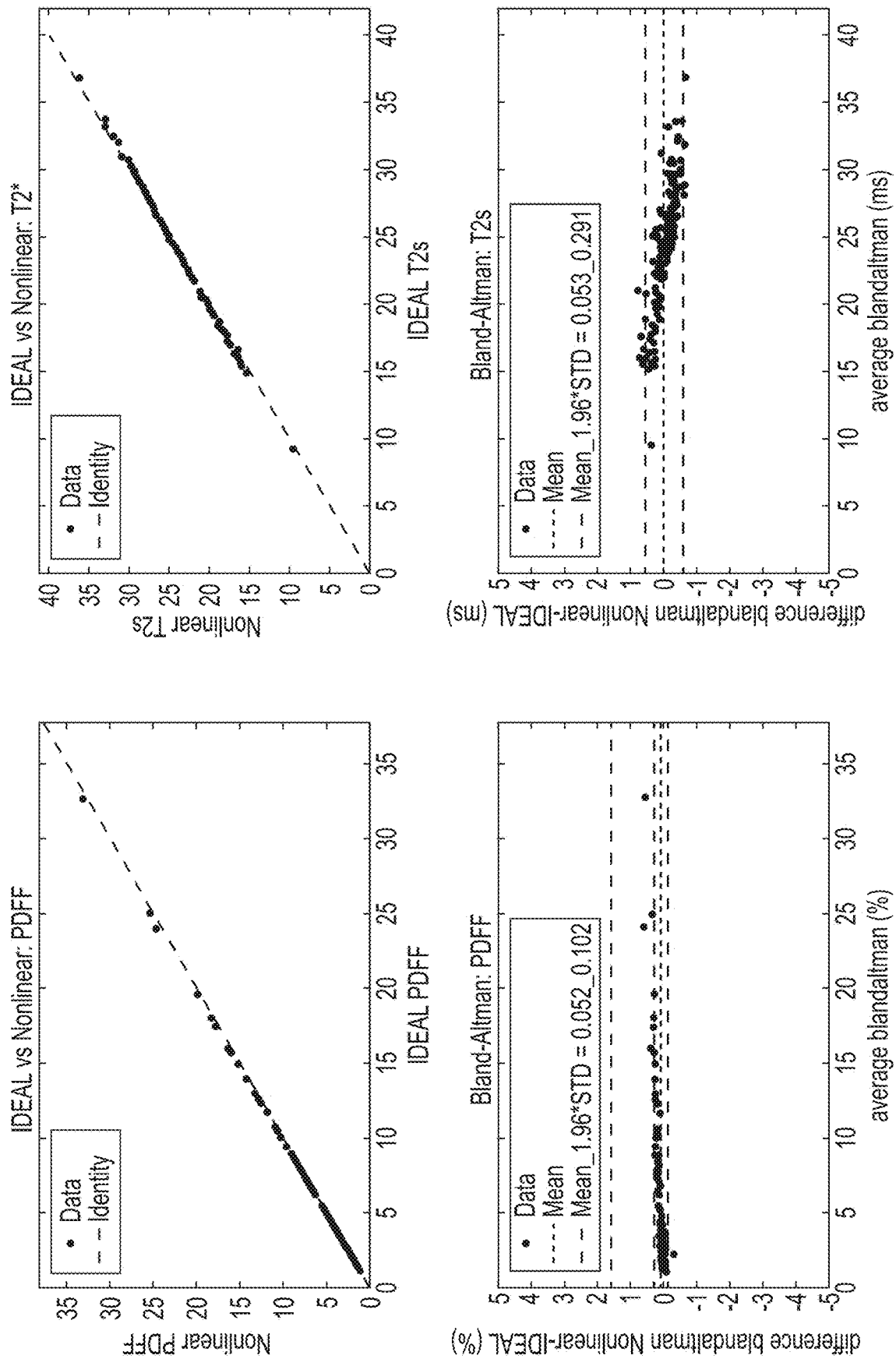
FIG. 10 shows the agreement (absolute and Bland Altman) between prior art measurements and measurements obtained using this invention.

Median values drawn from the magnitude-based PDFF and $T_2$* output maps were compared to the reference values. FIG. 10 shows absolute comparisons (top images) and Bland-Altman plots (lower images) for both PDFF and $T_2$* reported values. The 95% confidence intervals (CI) were calculated for the joined analysed cases. For PDFF, 95% CI were (0.052±0.102)%. For $T_2$*, 95% CI were (−0.053±0.291)%. Difference between complex based LMS IDEAL and the magnitude-based method was less than 0.5% PDFF points in all cases, and less than 1 ms $T_2$* in all cases.

Figure 11:
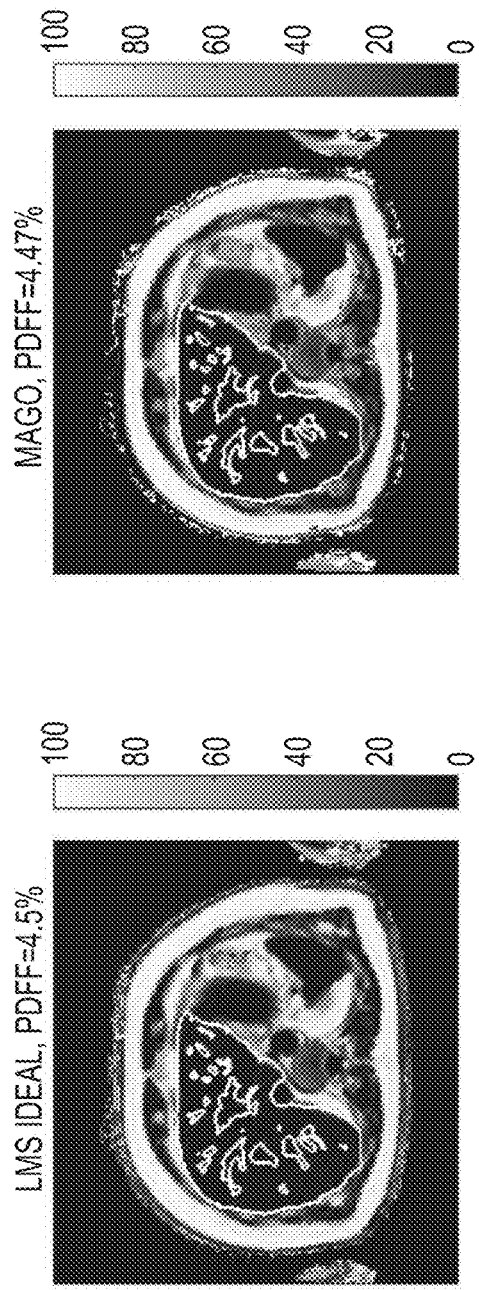
FIG. 11 compares MRI PDFF images obtained from prior art methods, and the method of this invention.
Figure 11:
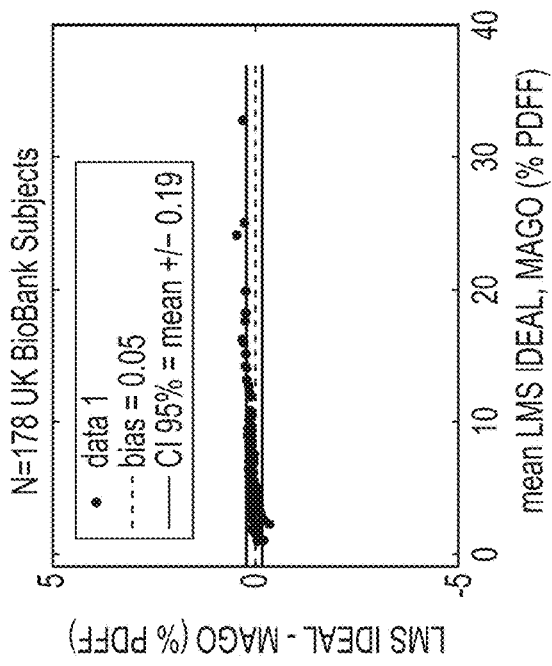
Figure 11:
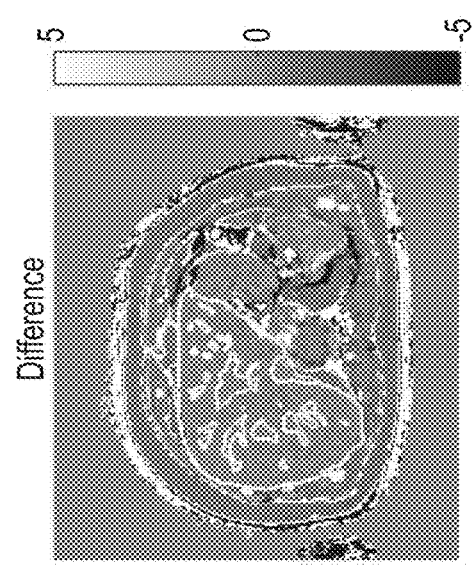

A typical set of images from the Biobank cohort are shown in FIG. 11, along with a Bland Altman plot for the PDFF measurements. The reference LMS IDEAL method image (left hand image a) is shown with the overlapped automatic segmentation mask. The magnitude-based method of this invention resulted in image (b). The difference image is shown as image (c). illustrating small (<1% PDFF) differences between the complex-based and the magnitude-based methods in the subcutaneous fat regions, demonstrating that the magnitude-based method of this invention was able to accurately estimate PDFF within the full dynamic range (0-100%). Note the smoothness prior on the fieldmap causes LMS IDEAL images to look smoother compared to the magnitude-based method images. The Bland-Altman plot (image 11(d)) comparing all N=178 median PDFF measures shows excellent unbiased agreement between reconstruction methods.

Figure 12:
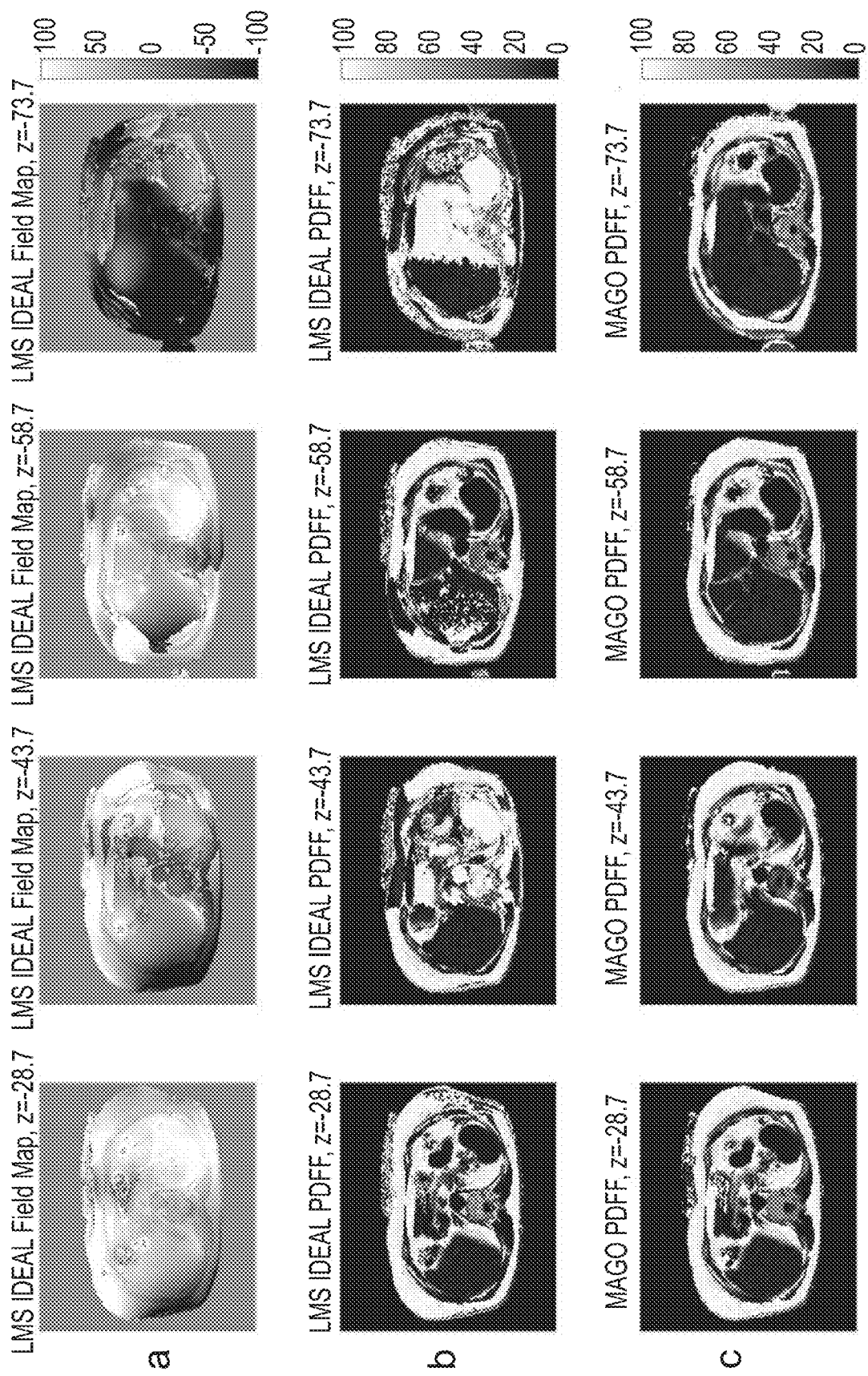
FIG. 12 shows field maps and MRI PDFF images for the prior art method, and MRI images obtained using the method of the invention.

FIG. 12 shows MRI PDFF images and fieldmaps obtained from a Philips Ingenia 3 T, multi-slice case from the Leiden site that presented substantial fat-water swap artefacts in LMS IDEAL caused by incorrect field map estimation, possibly due to unreliable phase information. This figure shows the effect of inconsistent phase information on field map estimation and subsequent PDFF maps calculation for the complex-based method LMS IDEAL.

Field map piece-wise convergence to local minima (row a) causes observable fat-water swap artefacts in the LMS IDEAL PDFF maps that are propagated throughout the images (row b), notably in the liver region and subcutaneous fat, but also in the spleen, the spine and the descending aorta. PDFF maps from MAGO (the method of this invention) show no evidence of fat-water swaps and are still able to resolve the magnitude-related water-fat ambiguity over the full dynamic range 0-100% (row c). The magnitude only method of this invention (bottom row) looks robust to such errors and was able to resolve the magnitude-related water-fat ambiguity in all slices.

Figure 13:
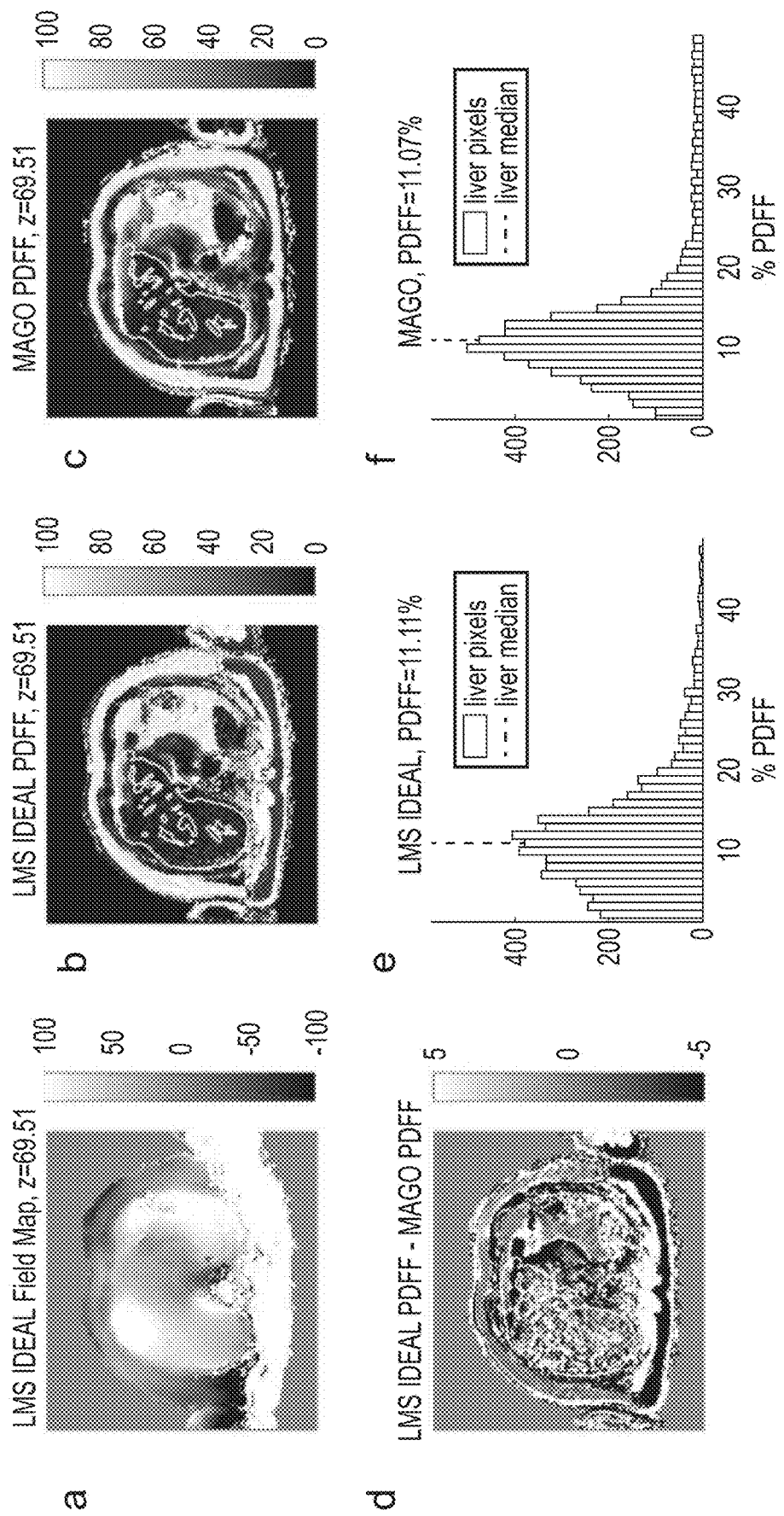
FIG. 13 shows field maps, MRI PDFF images and distributions obtained using the prior art method and the method of this invention.

FIG. 13 shows fieldmaps, MRI PDFF images, and distributions obtained from a Siemens TrioTim 3 T slice from the Coimbra site. This presented a fat-water swap artefact in the posterior area of subcutaneous fat in LMS IDEAL. Phase errors also seem to propagate into the liver, shown by the difference image (d) LMS IDEAL-MAGO, but may be imperceptible in many cases. We would expect a normally distributed histogram of PDFF values within the liver mask (FIG. 13 d, e), and a noisy distribution to present higher spread around the median value. While the reported median PDFF values from the automatic whole-liver segmentation agree (11.11% PDFF in LMS IDEAL, 11.07% PDFF in MAGO).

FIG. 13 also shows the effect of field inhomogeneity on the estimation of PDFF maps using LMS IDEAL and the magnitude only method of this invention. The field map image from the complex-based LMS IDEAL method (a) shows aliasing in the posterior area that reflects as a substantial fat-water swap artefact in the LMS IDEAL PDFF map (b), mainly affecting subcutaneous fat but also muscles and the left arm of the individual (right in the image). The PDFF map for the magnitude only method of this invention (c) shows no signs of fat-water swap artefacts and resolves PDFF over the full dynamic range 0-100%. Phase errors at a high field strength are reflected in the PDFF difference image (d) through a speckle pattern and a wider distribution of LMS IDEAL PDFF values within the liver mask (e) compared to the magnitude only distribution (f). A median whole-liver PDFF value is still quite robust to the observed variability in this case, demonstrated by the reported PDFF measures of the two methods (LMS IDEAL PDFF=11.11%, magnitude only method of the invention PDFF=11.07%).

Figure 14:
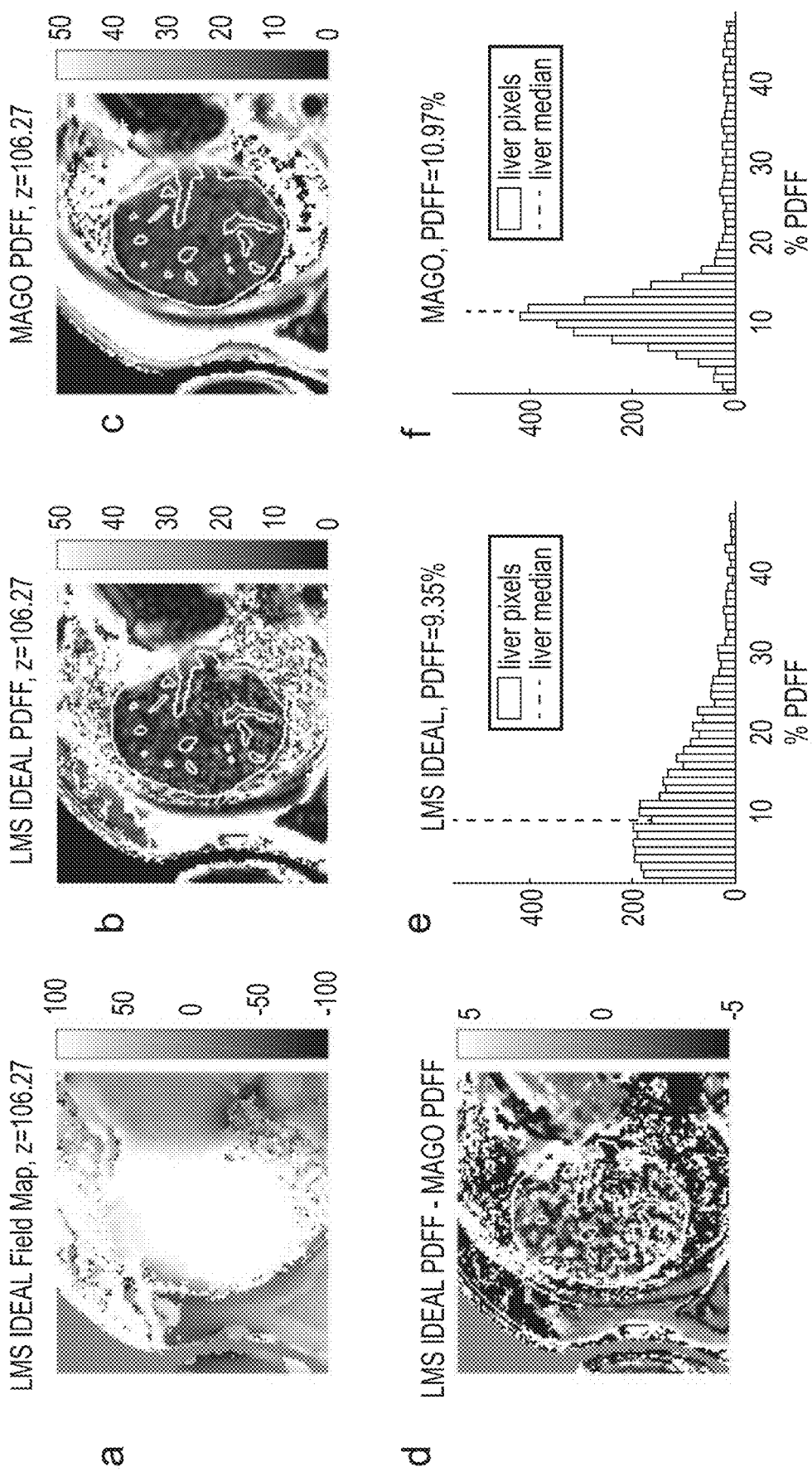
FIG. 14 shows field maps, MRI PDFF images and distributions obtained using the prior art method and the method of this invention.

FIG. 14 show the results from a superior slice of a RADIcAL case (Uniklinik, Siemens Skyra 3 T). The MRI PDFF images show the impact of field inhomogeneity and phase errors on the reported PDFF measures by the LMS IDEAL prior art method (images a and b) and the MAGO (magnitude only) method of this invention (image c).

High field map values from the complex-based LMS IDEAL method (a) cause a noisy pattern within the liver region in the LMS IDEAL PDFF map (b), which is less evident from the MAGO PDFF map (c). The method of this invention resolves the PDFF over the full dynamic range 0-100% but the plots (FIGS. 14(e) and (f)) have been rescaled to 0-50% to appreciate the local artefactual texture in the liver, which also shows in the difference image (d) and the histogram distributions of voxel intensities (e, f). The difference image (d) shows agreement where the field map has converged to lower values. It can be seen that the two distributions have the same total count of voxels, since they were drawn from the same automatic segmentation mask. The borders of the automatic segmentation mask were manually corrected in this case. The median whole-liver PDFF values differ substantially (LMS IDEAL PDFF=9.35%, MAGO PDFF=10.97%).

Note the magnitude only method of this invention does not apply smoothing at any stage of the processing, contrarily to smoothness constraints on the LMS IDEAL field map estimation step. In the prior art methods ambiguities may be approached by regularisation over a particular domain, whereas this is not needed for the method of this invention. Of course, this does not mean that spatial regularisation should not be used in association with the MAGO method of the invention; for example, it may be useful in low signal to noise cases. The results presented above for this invention have not used spatial regularisation in order to provide a "base case" of performance. Evidently, a more sophisticated spatial regularisation method could be added in the MAGO PDFF image, based for example on Markov Random Fields.

Generally fat (or other species) may be homogeneously distributed in an organ such as the liver, or may be heterogeneously distributed. If the species distribution is homogeneous, then an MRI PDFF image of a single slice through the organ will be representative for that species throughout the organ. However, if the species is heterogeneously distributed in the organ, then this may have clinical implications, and it is important to obtain accurate MRI PDFF images throughout the organ if the image will be used for clinical or surgical decisions. The method of this invention can be used to provide MRI PDFF images for multiple slices of an organ where the fat (or other species) is heterogeneously distributed.

In summary, the method of this invention has the following features. Firstly, the method only uses magnitude data: this reduces the number of variables to estimate, and the local minima to just two within the physiologically meaningful search space. The method also uses a multi-peak spectral model of at least one species: this enables resolution of the species ambiguity by displacing the aliased solution and reducing its associated cost function value. Also, the method uses a multi-point search step and comparing the cost function values at least two solutions: this enables exploration of both solutions using at least two sets of initial conditions.

MRI CSE methods have become increasingly important clinically for (a) robust water-fat separation—the inclusion of complete multi-peak fat models, compared to conventional Fat-Sat which are only able to target the main fat peak (70% relative amplitude)—, and (b) accurate liver fat fraction quantification for many applications. The non-invasiveness of CSE methods avoids the need for painful expensive biopsies and allow for imaging heterogeneous disease. This invention is for a magnitude-only CSE method which embodies a multi-peak spectrum for fat (or other species) and which can use flexible echo combinations to estimate PDFF across the entire dynamic range (0-100%). Unlike field map estimation, as used in complex-based PDFF estimates where the search algorithm has to contend with multiple local minima, and where an incorrect choice typically gives rise to fat-water swaps, we have shown that in general that this method has to choose between two local minima placed about 50% PDFF. Using 6-point phantom and 6- to 12-point clinical data, we have shown that the "correct" solution can be determined from the cost function values to two runs of the algorithm, for example one starting at 0%, the other at 100%.

As has been shown from the theory and simulated data described above, three necessary conditions are needed for the MAGO method of this invention to work. The first necessary condition implies the use of magnitude data only in order to reduce the multiple local minima that result from complex-based (phase and magnitude) methods to generally two local minima. It has been shown that the fieldmap search space from complex-based methods is not always periodic in the plausible range of fieldmap values (24), so using a multi-point method in complex-based methods may generally be less effective. Furthermore, convergence to wrong fieldmap solutions may not be readily apparent in PDFF maps, as 'double fat-water swaps' have been described, where reported PDFF values are incorrect but still in the feasible range. In general, using magnitude data alone ensures only two local minima have to be explored, and the appearance of possible mis-identification is more evident. Also, the use of magnitude data allows for direct estimation of PDFF, without the need of a field map estimation step nor typically used smoothness assumptions (29), which may not always hold. The second necessary condition involves the use of a multi-peak spectral model for one of the species (in this case, fat) in order to break the symmetry in the search space, so the two local minima have different cost function values and the magnitude-related water-fat ambiguity may be resolved (17). The third necessary condition relates to the use of a search space method to explore the two minima; a multipoint search technique was used hereby since previous information on the optimisation space is available: there will be a PDFF local minimum below 50% and another one above 50% in the general case. This ensures correct convergence when actual PDFF values are high and prevents convergence to local minima that has been observed in traditional magnitude-based methods. We note that there are many other potential search space techniques that may be used.

The availability of public phantom data and results allowed for the comparison of the new method to the implementation of the prior art IDEAL method. These experiments also enabled the assessment of the accuracy of the new magnitude-based method directly against ground truth phantom concentrations. The results show comparable accuracy of the MAGO method with respect to the prior art IDEAL method, in terms of slope, intercept, and r-squared agreement, and also showing overall reproducibility for the full dynamic range of PDFF values. The MAGO method of this invention is able to accurately resolve the magnitude-related fat-water ambiguity over the vials at 51.4% PDFF and at 100% PDFF. These reproducibility results suggest the potential of the MAGO method for in-vivo standardization across scanner manufacturers, acquisition protocols and field strengths.

We have noted throughout the experiments that the SNR benefits of high field MRI translate in the method of this invention to more robust and accurate PDFF estimates. This seems to be in contrast to complex-based PDFF estimation methods, whose apparently higher SNR is not found in clinical practice due to phase errors and high field variations. One reason why higher field strength benefits the method of this invention is that it enables more echoes to be used, resulting in higher confidence in the difference in the cost function values for the runs initialised at 0% and 100%. This in turn results in greater resolvability and accuracy of PDFF estimation.

As discussed above, previous methods using phase and magnitude data necessitates fieldmap estimation, and there are many local minima when using complex data and estimating the fieldmap (24), so a multi-point search approach is less feasible. In addition, If the exhaustive search step is not used, the converged solution of water and fat estimates will be dependent on their initial values in the iterative optimisation. In the case PDFF=0 is used as initial conditions, the result will always take PDFF<50% values (15) Finally, using a single-peak model will cause unresolvable ambiguity between the fat and water components.

A new magnitude-only method is presented that shows effectiveness in resolving fat-water ambiguity above 50% PDFF, and its accuracy is validated with multiple Biobank cases against a reference complex-based method, which uses both magnitude and phase information. The new magnitude-only based method is tested against a more challenging cohort, demonstrating similar accuracy and precision to the complex-based in cases where phase information is reliable. Furthermore, the new method presents increased robustness to errors (most of them in the phase images) that often cause complex-based methods in general to fail in clinical practice.

The method of this invention also allows spatial regularisation: generally, the fieldmap, which may be estimated following the estimation of the species (e.g. fat, water) using the method of this application, varies smoothly. The fieldmap can be used to assess image quality, including quantification of any artefacts.

The method of this invention provided MRI species separation. The formulation given in Equation (1) applies to many practical cases, the most of important of which is fat/water (proton density fat fraction estimation). The method described can also be used for artefact detection and estimation, and for estimation of iron content of the liver.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims. Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

REFERENCES

1. Younossi Z M, Koenig A B, Abdelatif D, Fazel Y, Henry L, Wymer M. Global epidemiology of nonalcoholic fatty liver disease-Meta-analytic assessment of prevalence, incidence, and outcomes. Hepatology 2016. DOI: 10.1002/hep.28431.
2. Williams C D, Stengel J, Asike M I, Torres D M, Shaw J, Contreras M, Landt C L, Harrison S A. Prevalence of nonalcoholic fatty liver disease and nonalcoholic steatohepatitis among a largely middle-aged population utilizing ultrasound and liver biopsy: a prospective study. Gastroenterology 2011. DOI: 10.1053/j.gastro.2010.09.038.
3. Caussy C, Reeder S B, Sirlin C B, Loomba R. Noninvasive, quantitative assessment of liver fat by MRI-PDFF as an endpoint in NASH trials. Hepatology 2018. DOI: 10.1002/hep.29797.
4. Szczepaniak L S, Nurenberg P, Leonard D, Browning J D, Reingold J S, Grundy S, Hobbs H H, Dobbins R L. Magnetic resonance spectroscopy to measure hepatic triglyceride content: prevalence of hepatic steatosis in the general population. Am J Physiol Endocrinol Metab 2005. DOI: 10.1152/ajpendo.00064.2004.
5. Dixon W. Simple proton spectroscopic imaging. Radiology 1984; 153: 189-194.
6. Glover G. Multipoint Dixon technique for water and fat proton and susceptibility imaging. J Magn Reson Imaging. 1991 September-October; 1(5):521-30. [PMID: 1790376].
7. Glover G H, Schneider E. Three-point Dixon technique for true water/fat decomposition with B0 inhomogeneity correction. Magn Reson Med. 1991 April; 18(2):371-83. [PMID: 2046518].
8. Xiang Q S, An L. Water-fat imaging with direct phase encoding. J Magn Reson Imaging. 1997 November-December; 7(6):1002-15. [PMID: 9400843].
9. Ma J, Singh S K, Kumar A J, Leeds N E, Broemeling L D. Method for efficient fast spin echo Dixon imaging. Magn Reson Med. 2002 December; 48(6):1021-7. DOI: 10.1002/mrm.10306.
10. Reeder S B, Wen Z, Yu H, Pineda A R, Gold G E, Markl M, Pelc N J. Multicoil Dixon chemical species separation with an iterative least-squares estimation method. Magn Reson Med. 2004 January; 51(1):35-45. DOI: 10.1002/mrm.10675.
11. Reeder S B, Pineda A R, Wen Z, Shimakawa A, Yu H, Brittain J H, Gold G E, Beaulieu C H, Pelc N J. Iterative decomposition of water and fat with echo asymmetry and least-squares estimation (IDEAL): application with fast spin-echo imaging. Magn Reson Med. 2005 September; 54(3):636-44. DOI: 10.1002/mrm.20624.
12. Hussain H K, Chenevert T L, Londy F J, Gulani V, Swanson S D, McKenna B J, Appelman H D, Adusumilli S, Greenson J K, Conjee-varam H S. Hepatic fat fraction: M R imaging for quantitative measurement and display—early experience. Radiology. 2005 December; 237(3): 1048-55. DOI: 10.1148/radiol.2373041639.
13. Yu H, McKenzie C A, Shimakawa A, Vu A T, Brau A C, Beatty P J, Pineda A R, Brittain J H, Reeder S B. Multiecho reconstruction for simultaneous water-fat decomposition and T2* estimation. J Magn Reson Imaging. 2007 October; 26(4):1153-61. DOI: 10.1002/jmri.21090.
14. Liu C Y, McKenzie C A, Yu H, Brittain J H, Reeder S B. Fat quantification with IDEAL gradient echo imaging: correction of bias from T(1) and noise. Magn Reson Med. 2007. DOI: 10.1002/mrm.21301.
15. Bydder M, Yokoo T, Hamilton G, Middleton M S, Chavez A D, Schwimmer J B, Lavine J E, Sirlin C B. Relaxation effects in the quantification of fat using gradient echo imaging. Magn Reson Imaging. 2008 April; 26(3):347-59. DOI: 10.1016/j.mri.2007.08.012.
16. Yu H, Shimakawa A, McKenzie C A, Brodsky E, Brittain J H, Reeder S B. Multiecho water-fat separation and simultaneous R2* estimation with multifrequency fat spectrum modeling. Magn Reson Med. 2008. DOI: 10.1002/mrm.21737.
17. Yu H, Shimakawa A, Hines C D, McKenzie C A, Hamilton G, Sirlin C B, Brittain J H, Reeder S B. Combination of complex-based and magnitude-based multiecho water-fat separation for accurate quantification of fat-fraction. Magn Reson Med. 2011. DOI: 10.1002/mrm.22840.
18. Cassidy F H, Yokoo T, Aganovic L, Hanna R F, Bydder M, Middleton M S, Hamilton G, Chavez A D, Schwimmer J B, Sirlin C B. Fatty liver disease: M R imaging techniques for the detection and quantification of liver steatosis. Radiographics 2009. DOI: 10.1148/rg.291075123.
19. Bley T A, Wieben O, François C J, Brittain J H, Reeder S B. Fat and water magnetic resonance imaging. J Magn Reson Imaging 2010 DOI: 10.1002/jmri.21895.
20. Haufe W M, Wolfson T, Hooker C A, Hooker J C, Covarrubias Y, Schlein A N, Hamilton G, Middleton M S, Angeles J E, Hernando D, Reeder S B, Schwimmer J B, Sirlin C B. Accuracy of PDFF estimation by magnitude-based and complex-based MRI in children with M R spectroscopy as a reference. J Magn Reson Imaging 2017. DOI: 10.1002/jmri.25699.
21. Noureddin M, Lam J, Peterson M R, Middleton M, Hamilton G, Le T A, Bettencourt R, Changchien C, Brenner D A, Sirlin C, Loomba R. Utility of magnetic resonance imaging versus histology for quantifying changes in liver fat in nonalcoholic fatty liver disease trials. Hepatology 2013. DOI: 10.1002/hep.26455.
22. Tyagi A, Yeganeh O, Levin Y, Hooker J C, Hamilton G C, Wolfson T, Gamst A, Zand A K, Heba E, Loomba R, Schwimmer J, Middleton M S, Sirlin C B. Intra- and inter-examination repeatability of magnetic resonance spectroscopy, magnitude-based MRI, and complex-based MRI for estimation of hepatic proton density fat fraction in overweight and obese children and adults. Abdom Imaging. 2015. DOI: 10.1007/s00261-015-0542-5.
23. Yokoo T, Bydder M, Hamilton G, Middleton M S, Gamst A C, Wolfson T, Hassanein T, Patton H M, Lavine J E, Schwimmer J B, Sirlin C B. Nonalcoholic fatty liver disease: diagnostic and fat-grading accuracy of low-flip-angle multiecho gradient-recalled-echo M R imaging at 1.5 T. Radiology 2009. DOI: 10.1148/radiol.2511080666.
24. Yu H, Reeder S B, Shimakawa A, Brittain J H, Pelc N J. Field map estimation with a region growing scheme for iterative 3-point water-fat decomposition. Magn Reson Med. 2005 October; 54(4):1032-9. DOI: 10.1002/mrm.20654.
25. Hernando D, Haldar J P, Sutton B P, Ma J, Kellman P, Liang Z P. Joint estimation of water/fat images and field inhomogeneity map. Magn Reson Med. 2008 March; 59(3):571-80. DOI: 10.1002/mrm.21522.
26. Hernando D, Kellman P, Haldar J P, Liang Z-P. Robust water/fat separation in the presence of large field inhomogeneities using a graph cut algorithm. Magn Reson Med. 2010 January; 63(1):79-90. DOI: 10.1002/mrm.22177.
27. Lu W, Hargreaves B A. Multiresolution field map estimation using golden section search for water-fat separation. Magn Reson Med. 2008 July; 60(1):236-44. DOI: 10.1002/mrm.21544.
28. Lu W, Lu Y. JIGSAW: Joint inhomogeneity estimation via global segment assembly for water-fat separation. IEEE Trans Med Imaging. 2011 July; 30(7):1417-26. DOI: 10.1109/TMI.2011.2122342.
29. Soliman A S, Yuan J, Vigen K K, White J A, Peters T M, McKenzie C A. Max-IDEAL: a max-flow based approach for IDEAL water/fat separation. Magn Reson Med. 2014 August; 72(2):510-21. DOI: 10.1002/mrm.24923.

30. Sharma S D, Artz N S, Hernando D, Horng D E, Reeder S B. Improving chemical shift encoded water-fat separation using object-based information of the magnetic field inhomogeneity. Magn Reson Med. 2015 February; 73(2): 597-604. DOI: 10.1002/mrm.25163.
31. Glover et al "three-point Dixon Technique for True Water/Fat Decomposition with B0 inhomogeneity correction" Magnetic Resonance in Medicine 1991, 18 p 371-383.
32. Yu et al., Robust Multipoint Water-Fat Separation Using Fat Likelihood Analysis 2012, Magnetic Resonance in Medicine 67, 1062-1076.
33. Hernando, Diego, et al. "R2* estimation using "in-phase" echoes in the presence of fat: the effects of complex spectrum of fat." Journal of magnetic resonance imaging 37.3 (2013): 717-726.
34. Zhong, Xiaodong, et al. "Liver fat quantification using a multi-step adaptive fitting approach with multi-echo GRE imaging." Magnetic resonance in medicine 72.5 (2014): 1353-1365.

The invention claimed is:

1. A method of analysing the magnitude of Magnetic Resonance Imaging (MRI) data from acquired MRI images to determine the relative signal contributions of at least two species to each voxel of the images, the method comprising the steps of:
using the magnitude of the multi-echo MRI data of images from the subject, where the images are acquired at arbitrarily timed echoes including at least one echo time where water and fat are not substantially in-phase with each other;
fitting the magnitude of said acquired multi-echo MM data to a single signal model to produce a plurality of potential solutions for the relative signal contributions for each of the at least two species from the model, by using a plurality of different starting conditions to generate a particular cost function value for each of the plurality of starting conditions, where said cost function values are independent of a field map term for the MRI data; and
analysing said cost function values to calculate the relative signal separation contribution for each species at each voxel of the images.

2. An image processing system arranged to analyse the magnitude of Magnetic Resonance Imaging (MRI) data from acquired MRI images to determine the relative signal contributions of at least two species to each voxel of the images, the image processing system comprising at least one processing device arranged to:
use the magnitude of the multi-echo MRI data of images from the subject, where the images are acquired at arbitrarily timed echoes including at least one echo time where water and fat are not substantially in-phase with each other;
fit the magnitude of said multi-echo MRI data to a single signal model to produce a plurality of potential solutions for the relative signal contributions for each of the at least two species from the model, by using a plurality of different starting conditions to generate a particular cost function value for each of the plurality of starting conditions, where said cost function values are independent of a field map term for the MRI data; and
analyse said cost function values to calculate the relative signal separation contribution for each species at each voxel of the images.

3. A method according to claim 1, wherein said analysis of said cost function values comprises the step of:
comparing the generated cost function values to determine which is the correct solution for said signal separation.

4. A method according to claim 3, wherein the lowest cost function value of said species is determined to be the correct solution for said signal.

5. A method according to claim 1, wherein said magnitude of said multi-echo MRI data is fitted to said single signal model using a model fitting algorithm.

6. A method according to claim 5, wherein said model fitting algorithm is an instance of at least one of the following: least squares estimation, iteratively reweighted least squares, least trimmed squares, or other robust approaches using m-estimators or s-estimators.

7. A method according to claim 5, wherein said model fitting algorithm is combined with at least one regularisation term.

8. A method according to claim 1, in which the single signal model includes a spectral model of one of the at least two species with more than one spectral component.

9. A method according to claim 1, wherein said single signal model includes at least one of the relaxation time quantities ($T_1$, $T_2$, $T_2^*$) to correct for signal decay.

10. A method according to claim 8, wherein the starting condition values of the relaxation time quantities are in the physically observable range.

11. A method according to claim 9, wherein the starting condition values of the relaxation time quantity $T_2^*$ are between 1 and 100 ms.

12. A method according to claim 9, wherein the starting condition values of the relaxation time quantity $T_2^*$ are between 10 and 30 ms.

13. A method according to claim 1, further comprising the step of using said species signal contribution to generate separate images showing the results for each species.

14. A method according to claim 13, in which one or more of the resulting images are post-processed.

15. The method according to claim 1, wherein the separated species contributions are used to estimate a field heterogeneity ('fieldmap') term.

16. The method according of claim 9, wherein the estimated relaxation time quantities are used to estimate a field heterogeneity ('fieldmap') term.

17. The method according to claim 1, wherein the at least two species include at least two of water, fat, hyperpolarized contrast elements or metabolites of such elements, markers for the presence of cancerous cells.

18. The method according to claim 1, wherein the subject includes a phantom model or animal or human tissue comprising at least one of the following organs: liver, pancreas, kidney, spleen, heart, muscle or adipose tissue.

19. The method of claim 1, in which cost function values in a certain voxel are used to update a likelihood map of the presence of at least one species in the voxel.

20. An image processing system as in claim 2, wherein the system is a non-transitory computer program product having executable program code stored therein, the program code operable for analysing the magnitude of magnetic resonance imaging (MRI) data.

* * * * *